Figure 1A:
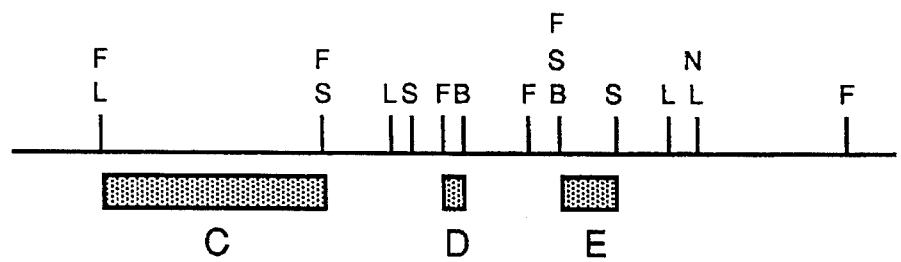

United States Patent [19]

Anand

[11] Patent Number: 5,525,467
[45] Date of Patent: Jun. 11, 1996

[54] NUCLEOTIDE SEQUENCES

[75] Inventor: Rakesh Anand, Sandbach, England

[73] Assignee: Imperial Chemical Industries PLC, London, United Kingdom

[21] Appl. No.: 255,889

[22] Filed: Jun. 7, 1994

Related U.S. Application Data

[63] Continuation of Ser. No. 899,067, Jun. 12, 1992, abandoned.

[30] Foreign Application Priority Data

| Jun. 13, 1991 | [GB] | United Kingdom | 9112795 |
| Jun. 13, 1991 | [GB] | United Kingdom | 9112797 |
| Jun. 13, 1991 | [GB] | United Kingdom | 9112799 |
| Jun. 13, 1991 | [GB] | United Kingdom | 9112801 |

[51] Int. Cl.$^6$ ................................ C12Q 1/68
[52] U.S. Cl. .................. 435/6; 435/7.1; 435/320.1; 435/172.3; 435/2
[58] Field of Search .............. 435/6, 7.1, 320.1, 435/172.3, 254, 255, 256, 254.1, 254.11, 254.2, 254.21; 536/23.1, 24.31, 24.2, 24.3, 24.33

[56] References Cited

FOREIGN PATENT DOCUMENTS

| 0341491 | 11/1989 | European Pat. Off. . |
| 0416801 | 3/1991 | European Pat. Off. . |
| 8903993 | 5/1989 | WIPO . |

OTHER PUBLICATIONS

St. George–Hyslop et al. 1987. Science 235, 885–890.
Stinissen et al. 1990 Genomics 7, 119–122.

*Primary Examiner*—Christopher S. F. Low
*Attorney, Agent, or Firm*—Cushman Darby & Cushman

[57] ABSTRACT

Yeast artificial chromosomes (YACs), nucleotide sequences and polypeptides derived therefrom. Their use in methods for the detection, diagnosis and therapy of Alzheimer's disease. Their use in the preparation of transfected cells and transgenic animals. Diagnostic kits for use in the methods of the invention.

11 Claims, 2 Drawing Sheets

NUCLEOTIDE SEQUENCES

This is a continuation of application Ser. No. 07/889,067, filed on Jun. 12, 1992, which was abandoned upon the filing hereof.

The present invention relates to yeast artificial chromosomes (YACs), nucleotide sequences and polypeptides derived therefrom; their use in methods for the detection, diagnosis and therapy of Alzheimer's disease. Particular aspects of the invention include nucleotide sequences coding for inherited disease associated genes such as Alzheimer's disease and to RNA such as mRNA, and polypeptides such as proteins and antibodies derived therefrom, all for use in diagnosis and therapy. The invention also relates to transfected cells and transgenic animals. Diagnostic kits are also provided for use in the diagnostic methods of the present invention. Alzheimer's disease is a lethal neurodegenerative disorder of unknown cause characterised at the clinical level by progressive dementia, unattributable to other causes, and, definitively at the histopathological level by the occurence of neuritic plaques and neurofibrillary tangles. The neuropathological features of Alzheimer's disease often develop in patients with Down's syndrome (DS) during their third and fourth decades. The latter is a genetic disorder caused by partial or complete trisomy of chromosome 21. In a minority of cases, Alzheimer's disease appears to be inherited as an autosomal dominant trait termed Familial Alzheimer's Disease (FAD).

In 1987, genetic linkage was detected between an FAD gene in four families and chromosome 21 markers with maximum lod scores for the loci D21S1/D21S11 and D21S16 (P. H. St George-Hyslop et al., Science, 1987, 235, 885–890). A major component of the neuritic plaques found in both DS and Alzheimer's disease is A4 protein or β amyloid protein, a 42 kd peptide derived from a larger polypeptide encoded by the Amyloid Precursor Protein (APP) gene on chromosome 21. The simplest hypothesis, to account for these findings, was that disruption of APP metabolism by gene dosage or other mutation may give rise to the dementia observed in DS or FAD respectively. This was refuted for the latter by two reports of recombination between FAD genes and APP in both the original (R. E. Tanzi et al., Nature, 1987, 329, 156–157) and additional FAD pedigrees (C. Van Broeckhoven et al., Nature, 1987, 329, 153–155). While some subsequent studies have excluded linkage of FAD to chromosome 21 (M. A. Pericak-Vance et al., Exp. Neurol., 1988, 102, 271–279; G. D. Schellenberg et al., Am. J. Hum. Genet., 1991, 48, 563–583), suggesting genetic heterogeneity, another found strongest linkage to the proximal marker 21S16 (A. M. Goate et al., Lancet i, 1989, 352–355). The issue of genetic heterogeneity in FAD was addressed in a large collaborative study of 48 pedigrees (P. H. St George-Hyslop et al., Nature, 1990, 347, 194–197). It was concluded that FAD is not a single homogeneous disorder. Families wih pre-senile onset (<65 years) of dementia showed strongest evidence of linkage to 21 q markers but the location of the FAD gene with respect to the markers D21S1/D21S11 and D21S13/D21S16 was less well defined than in the above study of Goate et al. In view of this body of data it was a surprise when an identical C to T nucleotide substitution, not seen in the normal population, was found in the APP gene of two unrelated families with pre-senile FAD (A. M. Goate et al., Nature, 1991, 349, 704–706). This mutation would result in a Val for Ile amino acid substitution close to the carboxy-terminus of the A4 or β amyloid peptide. The most compelling conclusion is that this rather conservative mutation is responsible for the development of FAD in these families, neither of which display recombination with the APP gene. To date, a few other mutations at this or other positions in APP have been reported but these occurred in very few chromosome 21-linked FAD families (Lucotte et al, Nature, 1991, 351, 530; Murrell et al, Science, 1991, 254, 97–99).

The need therefore exists for further methods of diagnosis and therapy of Alzheimer's disease.

The present invention now provides yeast artificial chromosomes (YACs) which comprise gene sequences for Alzheimer's disease. Nucleotide sequences comprised in these YACs may be used in the detection of inherited or acquired disease alleles especially in the diagnosis and therapy of Alzheimer's disease.

The yeast artificial chromosomes of the present invention are hereinafter designated YAC 23CB10, YAC 28CA12 and YAC 26FF3. These were deposited with the National Collection of Industrial and Marine Bacteria (NCIMB), P. O. Box 31, 135 Abbey Road, Aberdeen AB9 8DG, Scotland prior to the filing of the patent applications from which this application claims priority. The NCIMB accession number of YAC clone SC/23CB10 is 40255 and its insert size is 425 kilobases. The NCIMB accession number of YAC clone SC/28CA12 is 40416 and its insert size is 270 kilobases. The NCIMB accession number of YAC clone SC/26FF3 is 40415 and its insert size is 220 kilobases. Each of the above YACs and its uses, whether taken alone or in combination with one or both of the other YACs represents an independent and particular aspect of the present invention.

In a first aspect of the present invention we provide a method for the detection of one or more inherited or acquired disease alleles in sample nucleic acid from an individual which method comprises determining the presence or absence of variant nucleotide sequence in a gene comprised in any one of YAC 23CB10, 28CA12 and 26FF3.

The inherited or acquired disease is conveniently Alzheimer's disease, or a condition leading to the development of such disease.

Therefore in a further aspect of the present invention we provide a method for the detection of one or more Alzheimer's disease alleles in sample nucleic acid from an individual which method comprises determining the presence or absence of variant nucleotide sequence in a gene comprised in any one of YAC 23CB10, 28CA12 and 26FF3.

A particular form of Alzheimer's disease which may be detected using the method of the present invention is pre-senile (<65 years) Alzheimer's disease.

The method of the present invention may also be useful for the detection of one or more senile onset Alzheimer's disease alleles in sample nucleic acid from an individual.

An allele is defined as a variant of a genetic locus and is inherited according to conventional principles of genetic segregation. An allele of a genetic locus may be characterised according to its size or composition or both size and composition. It will be appreciated that allelic variation at a genetic locus may result from insertion, deletion or rearrangement of, for example, many kilobases of nucleic acid, or variation may result from as little as a single base pair alteration. Any such variation at a genetic locus can be readily detected using methods known in the art. Whilst we do not wish to be bound by theoretical considerations it is believed that Alzheimer's disease may arise from deletion, insertion, rearrangement and point mutation events within gene(s), or gene controlling elements within or adjacent to gene(s) comprised in any one of YAC 23CB10, 28CA12 and 26FF3.

It will be understood that the expression "in a gene comprised in any one of YAC 23CB10, 28CA12 and 26FF3" includes coding and non-coding regions of a gene, at least a part of which is comprised within any one of YAC 23CB10, 28CA12 and 26FF3, as well as flanking regions of up to 100 kilobases, up to 75 kilobases, up to 50 kilobases, up to 25 kilobases, up to 20 kilobases, up to 15 kilbases, up to 10 kilobases and up to 5 kilobases.

Informative variation within a genetic locus may arise from variation within a disease associated gene itself or within a nucleotide sequence at a distance from but genetically linked to the disease associated gene. In general, diagnosis of variations within the disease associated gene itself is preferred as this eliminates the possibility that genetic recombination events have occurred which compromise the usefulness of the linked genetic marker. Similarly, as many acquired variations are deletion events of variable size and location variation within the disease associated gene itself increases the probability that such acquired variations will be detected. Informative variation at a linked genetic marker may conveniently arise from the presence of a variable number of tandem repeats of a nucleotide sequence. Examples of such regions include minisatellite regions wherein a nucleotide sequence of for example up to 50, 40, 30, 20, or up to 10 bases is repeated, for example as described in Am. J. Hum. Genet., 43, pages 854–859 (1988) by Nakamura et al, or a microsatellite region wherein a nucleotide sequence of up to 5, 4, 3, 2 or 1 base(s) is repeated, for example dinucleotide repeats such as (CA)n repeats or regions complementary thereto as described in Am. J. Hum. Genet., 44, pages 397–401, (1989), Litt et al and Am. J. Hum. Genet., 44, pages 388–396, (1989), Weber et al. Alternatively informative variation may arise from changes which affect sample nucleic acid cleavage, for example changes in the nucleotide sequences recognised by restriction enzymes. Such changes are conveniently detected as restriction fragment length polymorphisms (RFLPs) or may be identified using any other method for the detection of sequence variation.

In a convenient aspect of the present invention we provide a method for the detection of one or more inherited or acquired disease alleles in sample nucleic acid from an individual which method comprises determining whether or not an allele of a gene comprised in any one of YAC 23CB10, 28CA12 and 26FF3 in sample nucleic acid from a member of the individual's family has been inherited in a manner consistent with the presence of an inherited or acquired disease allele in sample nucleic acid from the individual to be tested.

Acquired disease alleles may be conveniently detected by determining whether or not allele(s) of a gene comprised in any one of YAC 23CB10, 28CA12 and 26FF3 in sample nucleic acid from an individual are acquired either in a manner inconsistent with alleles from a member of the individual's family or are acquired in only some nuclei of cells in the body. The former may be conveniently effected by analysis of nucleic acid from an individual and members of the individual's family, preferably the individual's parents, and observing alleles in the individual which are not present in either of the parents or other members of the individual's family. The latter may be conveniently effected by analysis of nucleic acid from different cells of an individual, for example from different cell types (tissues). Comparisons between the nucleic acid from the different regions of an individual's body then determine whether or not allele(s) of a gene comprised in any one of YAC 23CB10, 28CA12 and 26FF3 in the sample nucleic acids are different in the different regions, tissues or cell types, in a manner consistent with the presence of an acquired disease allele in part of the individual.

The method of the present invention is conveniently effected by determining the presence or absence of variant nucleotide sequence at a genetic locus comprised in a nucleic acid fragment to which a polynucleotide or its complement independently selected from any one of selectively hybridises.

| 23CB10L | | | | | | | |
|---|---|---|---|---|---|---|---|
| GGGATATTCA | ATTCAATTGA | GATTTGAGTG | GGGACCAAAC | CATATCAGGC | CCTGAATATC | | 60 |
| AGCCTCCAAA | TCAGCCAACT | TCTGATTATT | TACAGGANGG | CCTA | | | 104 |
| 23CB10R | | | | | | | |
| AAGTCTTGGT | TTCCTTNAAC | ATCTTTGTGC | CATCTCAAAT | CTGAATATTA | GGTATTGTCA | | 60 |
| CCCTACTACC | CATCAGGAGT | CCAGTGGTCT | TTCTCTCCTT | CTGCCATCA | | | 109 |
| 17BF9R | | | | | | | |
| TTANCGACAG | GAGACGNNTG | ACCATTATAA | NNGAGACACA | AAGAGACACC | GTTATGCATG | | 60 |
| GTGTAGAAAT | CGTGTACTAT | ACCGATAANT | TTACTCTTAC | GAAAACCTCA | TGAACTTTTA | | 120 |
| TANCTNTTCC | TTAAGGCNTT | AGANNNCTNN | NNCG | | | | 154 |
| 28CA12R | | | | | | | |
| GAATTCAGTT | NNAAATATGT | TGAGATTGAA | GTACAAAAAC | ATAGACATCT | CCAGGAGGTG | | 60 |
| TTTCCATGAA | AGAGACATGG | TGGGAAAAGT | AAATTTGTTG | ATGAGGTGGT | CCTTGAAGCC | | 120 |
| AG | | | | | | | 122 |
| 26FF3L | | | | | | | |
| GAATTCAGTC | AAGGATGACG | ATTGACAAAG | GAGTCTTATC | ATTTAAAAAA | TCATTTCAAA | | 60 |
| TTAAAGCTAA | TATCTTTTAA | GTATAGAAGT | AGACACAATA | AAATCATGTG | TAC | | 113 |
| 26FF3R | | | | | | | |
| GAATTCTTAA | AAGTGAATCA | TATAACCTAG | CCATTGTATT | TCTAAGTAGT | TATCCAAAAT | | 60 |
| ACCTGGAAGC | ATATTTCTGT | ACAAAAAATG | AGTTCATAAA | TGTTAATTGT | TTTATTTGTA | | 120 |
| ATAGCT | | | | | | | 126 |

Each of the above nucleotide sequences, and nucleic acid fragments to which it selectively hybridises, represents an independent and particular aspect of the present invention.

Convenient primers for the preparation of nucleotide sequences at the above loci are indicated in Table 1 set out hereinafter.

We have also identified and sequenced three HTF islands within the region spanned by YAC 28CA12. Therefore in a particular aspect the method of the present invention is effected by determining the presence or absence of variant nucleotide sequence at a genetic locus comprised in a nucleic acid fragment to which a polynucleotide or its complement independently selected from any one of selectively hybridises.

Any of the above methods are conveniently effected by contacting sample nucleic acid with polynucleotide(s) capable of distinguishing disease alleles in a gene comprised in any one of YAC 23CB10, 28CA12 and 26FF3 whether inherited or acquired. The polynucleotides are for example selected for performing any aspect of the method of the invention as set out hereinbefore.

3EH12A1

| | | | | | | |
|---|---|---|---|---|---|---|
| CGGGCCTGCT | TACTACAGGC | GCCCCGGCCA | TGGCCAGGCC | ATCGACACGG | CTGCCATCGA | 60 |
| AACGGCCACC | GCGTCAAGGG | CAGCTACAAC | CGGGCGGAAA | ACGTCTTCAA | GGTCAGCAAG | 120 |
| CCACGCGACG | ACGTGAAGAT | C | | | | 141 |

3EH12A7

| | | | | | | |
|---|---|---|---|---|---|---|
| GGTGATGCCG | TGCTCCTCCA | TCATGCTGGC | GGCATCCACG | GCCAGCGCGT | CTTCGGCGAT | 60 |
| GGTGCGTGGC | CCCTTGTGCA | TGACATCGCC | GGCCTGCAGC | GCGCGCAGGT | CGGTGCCGGC | 120 |
| CTCCACGCGG | CGGCGCAGGT | CTCCGTCGGT | GAAGATGCCC | TGCAGCACGC | CTGCCGCATC | 180 |
| GACGATGGCC | GAGCAGCCCA | GGCCCTTGGC | GCTCATCTCG | CGCATCAGTT | CGACAAAGCT | 240 |
| GGCATCNCCC | GACCTTCGGC | AGCTCATCGC | CGCTGCGCAT | GACATCACGC | ACATGGGTCA | 300 |
| GCAGTTTGCG | GCCCAGCGCA | CCGCCCGGAT | GGAGCGCGCA | AA | | 342 |

3EH12A7R

| | | | | | | |
|---|---|---|---|---|---|---|
| GATCCACGCC | GGCACCAGCC | TCTGAATTCC | CTTAGTATTT | ATTGATCTGG | GCATGGTGAC | 60 |
| CGGCATCGAC | CTGGTGCTGG | CGCTGTCCAA | CAGCGGCGAG | GCNATGACCT | CGCTGCGCTG | 120 |
| CTGCCGGCCA | TCAAGNCGAC | CAGGGCATAC | CCCTGGTGGC | CATGACCGGC | GGCGCGCAAT | 180 |
| CCACNCTNNC | NCGCCATGCT | GACTGGGTGC | TGGACACCGT | GTCGAGCNCG | AGGCCTGCCT | 240 |
| TTGAACCTGG | CA | | | | | 252 | or

3EH12C6

| | | | | | | |
|---|---|---|---|---|---|---|
| GATCTGTTCG | CCAATGTGCG | CGGCGCACGC | CTGCCGGCCT | GCACGCGGAA | ACCGTGCTCG | 60 |
| ATGGCCGTGG | GTTGGGCAAG | GTGCTGAAGC | GCTATCGGAT | TGCGTGAACC | ACTGCAGAGC | 120 |
| CGAGCATAGG | CTTATGGGGA | ATCCGCAGCA | ACGGGGTCAG | AGCCCTCTCC | ACAGGAGAGG | 180 |
| AATCCGACCC | CAGCGCGATG | AGCCGAGCAT | AGGCTCGTAC | GGGGAATCCG | CAGCAACGGG | 240 |
| GTCAGAGCCT | CTCCACAGGA | GAGGAATCCG | ACCCCAGCGC | GANAGGCATA | GGCTCGGCTC | 300 |
| TACGGGGAAT | CCGCAGCAAC | GGGGTCAGAG | NNCTCTCCTC | AGGAGAGGCA | TCCGACCCCG | 360 |
| GCGCCAGGGC | TTCAGCGCGC | | | | | 380 |

Each of the above nucleotide sequences, and nucleic acid fragments to which it selectively hybridises, represents an independent and particular aspect of the present invention.

By the expression "selectively hybridises" we mean that in a mixture of nucleic acid fragments, produced for example by the action of one or more restriction enzymes on a YAC of the invention, and under appropriate hybridisation conditions, the polynucleotide hybridises to and thus identifies the nucleic acid fragment.

Convenient nucleic acid fragments include those produced by the action of restriction enzymes on the YAC of the invention such as BssHII, SacII, EagI, NaeI, SfiI or XhoI. Further convenient fragments include those produced by the action of Sau3A1, TaqI, AluI, HinfI, RsaI, EcoRV, SspI, HincII and StuI as well as EcoRI, PstI, BamHI, HindIII, PvuII or KpnI. Particular nucleic acid fragments are produced by the action of NaeI. Further particular nucleic acid fragments are produced by the action of XhoI.

Independent and particular aspects of the present invention are comprised by single nucleic acid fragments to which one of the nucleotide sequences specifically indicated above selectively hybridises and wherein the single nucleic acid fragment is produced by the action of a single restriction enzyme as indicated immediately above.

Further independent and particular aspects of the invention comprise determining the presence or absence of variant nucleotide sequence at a genetic locus comprised in a single nucleic acid fragment as defined above.

The polynucleotide(s) may be capable of distinguishing alleles of a genetic locus comprised in the gene, for example either as polynucleotide probes or as primers for possible extension. The polynucleotide(s) can be DNA, RNA or any other kind hybridisable to DNA. The polynucleotide(s) are conveniently DNA. The nucleic acid can be in double stranded or single stranded form, conveniently single stranded and may include modified bases such as hypoxanthine or deazaguanine such as 7-deazaguanine.

The polynucleotide probes can be prepared by microbiological reproduction of cloned material or by direct synthesis. The probe may include label or marker components and is then conveniently $^{32}P$ radiolabelled in any conventional way, but can alternatively be radiolabelled by other means well known in the hybridisation art for example to give $^{35}S$- or $^{33}P$-radiolabelled probes. The nucleotide may also be labelled with non-radioactive species such as biotin or a similar species by the method of D. C. Ward et al, as described in Proceedings of the 1981 ICN-UCLA Symposium on Developmental Biology using Purified Genes held in Keystone, Colo. on Mar. 15–20, 1981 vol. XXIII, pages 647–658, Academic Press; Editor Donald D Brown et al, or even enzyme labelled by the method of A. D. B. Malcolm et al, Abstracts of the 604th Biochemical Society Meeting, Cambridge, England (meeting of 1 Jul., 1983. Further and particularly convenient methods of non-isotopic labelling are described in our European patent application, publication no. 0207758.

The polynucleotide probes may hybridise selectively under appropriate conditions to different alleles of a genetic locus. Suitable hybridisation conditions will depend on the relevant nucleotide sequences but can be readily determined by the skilled man, for example after appropriate routine experimentation. Thus, for example, the polynucleotide sequences may be complementary to either variant nucleotide sequences indicative of one or more Alzheimer's disease alleles or to nucleotide sequences indicative of normal alleles. Dot Blot hybridisation provides a convenient method for the detection or absence of a hybridisation product.

Polynucleotide probes as outlined above comprise a further aspect of the present invention. Their nucleotide sequence is of any convenient length such as up to 50, 40, 30 or 20 nucleotides, for example comprising at least 6, 8, 10, 12, 14, 15, 16 or 18 nucleotides. Conveniently their nucleotide sequence comprises 10–25, 15–20, 17–19 or 18 nucleotides. It will be appreciated that longer nucleotide sequences may require the inclusion of destabilising nucleotides. Appropriate sequences may be determined by routine experimentation.

Sample genomic DNA may be fragmented for example using enzymes such as restriction enzymes prior to hybridisation with probe(s). The nucleic acids may then be separated according to molecular weight and conveniently using gel electrophoresis for example on a solid support. Hybridisation with probe(s) is then carried out, for example using Southern Blot hybridisation (E. M. Southern, J. Mol. Biol, 1975, 98, 503–517. Where the probe used is radiolabelled, autoradiography is a convenient method of detection. Alternatively, any convenient non-radioactive detection system may be employed.

If required the sample genomic DNA may be amplified. Extension of a nucleic acid primer on a DNA or RNA template provides an extension product comprising a nucleotide sequence complementary to the nucleotide sequence of the relevant DNA. Convenient amplification methods include polymerase mediated chain reactions such as those disclosed by K. Kleppe et al in J. Mol. Biol., 1971, 56, 341–361 and in U.S. Pat. Nos. 4,683,195 and 4,683,202 or alternatively Q-beta replicase as described in PCT Patent application, publication WO-87/06270 and in Biotechnology, Vol 6, October 1988 may be used. Additionally transcription based nucleic acid amplification described in PCT Patent application, publication WO-88/10315 (Siska Corporation) may be used. Further amplification methods include the use of thermostable DNA ligase. Alternatively linear amplification, as opposed to exponential amplification for example as obtained via the polymerase chain reaction, may be used. In linear amplification a polynucleotide primer anneals to a sample DNA template, under appropriate conditions the primer is extended as far as required and the extension product is then separated from the template. The above process of primer annealing, extension and separation is repeated as many times as required. It will be appreciated that since primer extension always occurs on a sample DNA template the possibility of inaccurate copies being formed is reduced. The number of cycles required in respect of linear amplification will generally be higher than that for exponential amplification. Generally a primer will comprise at least seven nucleotides, such as at least 10, 15 or 20 nucleotides, for example 15–40 or 20–30 nucleotides. The maximum length of any primer is not believed to be critical and is only limited by practical considerations.

As mentioned previously polynucleotide(s) may be capable of distinguishing alleles of the genetic locus when acting as primers for possible extension. Appropriate primers are prepared as for sample DNA amplification as described above.

Alleles of a genetic locus are conveniently detected using the amplification refractory mutation system (ARMS) as described by Newton et al in Nucleic Acids Research, 17, 7, 1989, pages 2503–2516 and claimed in our European Patent Application, Publication No. 0332435. ARMS employs a diagnostic primer substantially complementary to a diagnostic region so that under appropriate conditions the identity of a terminal nucleotide being either a normal or variant nucleotide may be detected by reference to the formation or non-formation of an extension product. The expression "diagnostic portion" means that portion of a target base sequence which contains a nucleotide as its terminal nucleotide the potential variant nucleotide, the presence or absence of which is to be detected.

Extended primers may be detected not only by the use of appropriate probes but also by direct methods not requiring the use of probes, for example products of a given size may be directly visualised or products may firstly be separated according to molecular weight for example using gel electrophoresis prior to detection, for example by visualisation.

Diagnostic primers may be used in any appropriate aspect of the present invention. Additionally an amplification primer corresponding to each diagnostic primer is preferably provided the nucleotide sequence of the amplification primer being such that any extension product of the corresponding diagnostic primer may, after separation from its complement, serve as a template for synthesis of an extension product of the amplification primer.

Extension products as produced above may then be amplified using any convenient technique such as those mentioned above in respect of sample DNA amplification.

It will be understood that different genetic loci may be detected simultaneously or sequentially. Appropriate probes and/or primers are employed in respect of each genetic locus to be analysed. By way of example multiple polymerase chain reactions (PCRs) may be performed in the same reaction vessel. Primers spanning all coding regions or key coding regions of a gene may be used. An example of the use of such a process for the detection of mutations associated with Duchenne muscular dystrophy is known (J. S. Chamberlain et al, 1988, Nucl. Acids. Res., 16, 11141–11156). Mutation may be observed in the amplification products, for example by observing the pattern, sequence or intensity of the products in particular after gel electrophoresis separation. Amplification is performed on any convenient nucleic acid template such as DNA or RNA.

Conveniently the amplification refractory mutation system (ARMS) as described by Newton et al in Nucleic Acids Research, 17, 7, 1989, pages 2503–2516 and claimed in our European Patent Application, Publication No. 332435 may be employed to distinguish alleles of each locus of interest.

The polynucleotide probes or diagnostic primers of the present invention may be provided in a kit together with appropriate instructions and/or inserts and conveniently together with test or control DNA. These comprise further aspects of the present invention.

In respect of diagnostic primers the kit will conveniently comprise a diagnostic primer for each diagnostic portion of a target genomic DNA sequence together with each of four different deoxy nucleoside triphosphates; and an agent for polymerisation of the deoxy nucleoside triphosphates. Preferably the kit of the present invention additionally comprises an amplification primer corresponding to each diagnostic primer the nucleotide sequence of the amplification primer being such that any extension product of the corresponding diagnostic primer may, after separation from its complement, serve as a template for synthesis of an extension product of the amplification primer. Each of the materials detailed above and/or the amplification primer may be conveniently packaged in a separate container, but preferably all may be combined in a single container to which the material to be analysed is added. Advantageously the single container will additionally contain buffer.

Alleles of a genetic locus may alternatively be detected by direct nucleotide sequencing, for example of PCR products. As mentioned earlier above, methods and materials for carrying out nucleotide sequencing will be immediately apparent to the molecular biologist of ordinary skill, for example using methods analogous to those outlined in Nucleic Acids Research, 16, 8233–8243, 1988, Newton et al; and Nature, 1988, 332, 543–546, Higuchi et al.

As described above one important application of the present invention is the identification of a previously unidentified genotype, for example a genetic defect(s) responsible for a phenotype, for example a genetic disease or disorder or the identification of a previously unidentified genotype, for example a genetic defect(s) which is (are) responsible for or a contributory factor in predisposition to a phenotype, for example a disease.

Thus for example in relation to a genotype such as a genetic disease or disorder the method of the present invention may be applied to nucleic acid which does not contain the genotype (e.g. genetic defect(s)) and to nucleic acid which does contain the genotype e.g. genetic defect(s) to be investigated, identification of the genotype e.g. genetic defect(s) being effected by comparison of the information generated by sequencing of the two nucleic acid samples. Such comparison may be effected, for example, by comparison of the sequencing gels conveniently by automatic scanning. In this regard it will be appreciated that the specific sequences need not be determined per se provided that sufficient data is generated to enable a difference or differences between the target nucleic acid samples to be detected and identified, and the terms "sequencing" and "sequenced" are accordingly used herein to include not only specific nucleotide sequence determination, but also the detection and identification of sequence differences without specific nucleotide sequence determination. It is convenient to apply the method of the invention to the target nucleic acid of an obligate heterozygote for example for the genetic disease or disorder to be investigated. Of necessity both a normal and a mutant allele for the locus in question will be present in such an individual and those sites identified using the method of the invention where more than a single nucleotide is present on sequencing are candidates to be the phenotype, e.g. disease or disorder causing mutation.

In addition it will be appreciated that nucleic acid which contains the genotype, for example genetic defect(s), may be detected by analysis of heteroduplex molecules. For example genetic variation may be detected by formation of heteroduplex molecules preferably following amplification and subsequent analysis by a method which will distinguish mismatched from perfectly matched heteroduplex molecules. Such methods may involve the use of enzymes such as RNAse-A for example as described by M. Myers et al, 1985, Science, 2.30, 1242; chemical recognition of mismatches such as with the use of hydroxylamine or osmium tetroxide (A. J. Montanilon et al, 1989, Nucl. Acids. Res., 17, 3347–3358) or detection of altered physical properties as in the use of denaturing gradient gel electrophoresis (R. M. Myers et al, 1985, Nucl. Acids. Res., 13, 3131). These methods provide additional means whereby sequence differences can be detected without prior knowledge or specific sequence determination.

In addition to the above it is suspected that certain genotypes e.g. genetic defects whether local or throughout the body may predispose individuals to phenotypes. For example, if such genetic defects could be identified then such defined "risk" patients could be monitored and any onset or progression of the disease treated at an early stage. The method of the present invention may be applied to the identification of such predisposing genotypes. Comparison of sequence differences between different patient and cell type classifications may identify the presence of any predisposing genotype or genotype/phenotype correlation. Comparison of nucleotide sequences of Alzheimer's disease genes from affected and unaffected individuals allows the characterisation of all of the different mutations responsible for Alzheimer's disease.

A further aspect of the present invention comprises the use of the yeast artificial chromosome of the present invention, for example as a hybridisation probe for example for the detection of inherited or acquired disease alleles. Probes may be conveniently provided by the removal of repetitive sequences from the chosen YAC nucleotide sequence. Removal of repetitive sequences is conveniently acomplished by reassociation for example in the presence of excess human DNA (Sealey et al, Nucleic Acids Research, 1985, 13, 1905–1922). Thus for example nucleotide sequences comprised in the YAC may be used as hybridisation probes to detect inherited or acquired disease alleles in sample DNA for example on Southern blots prepared from gels.

Therefore according to a further aspect of the present invention there are provided nucleotide sequences of at least 1 kilobase, 3 kilobases, 5 kilobase, 7 kilobases, particularly 10 kilobases, 50 kilobases, 100 kilobases, 200 kilobases, 250 kilobases, 300 kilobases, 350 kilobases, 400 kilobases or up to 425 kilobases comprised in any one of YAC 23CB10, 28CA12 and 26FF3 for use as a hybridisation probe. The probe is conveniently prepared by the action of a restriction enzyme as hereinbefore indicated or any convenient combination thereof. The nucleotide sequence may have an optional label or marker component when used as a hybridisation probe.

Characterisation of the YAC of the present invention to identify regions of diagnostic and therapeutic interest may be carried out using any one of or convenient combination of the following techniques.

An important approach is the use of the invention described in our European patent application, publication no. 356021 and incorporated herein by reference, to characterise the nucleotide sequence of any one of YAC 23CB10, 28CA12 and 26FF3 of the present invention. The invention claimed in EP-A-356021 is referred to hereinafter as Chemical Genetics and relates to a method for the amplification of nucleotide sequences. Such a method is of particular interest in relation to the amplification of sequences only a portion of which is known and enables long nucleotide sequences to be rapidly and efficiently sequenced. The method avoids the recombinant DNA cloning procedures hitherto necessary for the sequencing of unknown nucleotide sequences. By so doing it also allows polymorphisms between nucleotide sequences of different alleles at a genetic locus to be detected as well as the simultaneous analysis of alleles at a particular locus in different individuals. The prior art technique of "chromosome walking" involves a number of potential difficulties as is exemplified by the time taken from discovery of a marker for a genetic disorder to discovery of the specific genetic lesion responsible for the disorder. Thus, for example, a linked genetic marker for Huntington's Chorea (D4S10) was discovered in 1983, but still today the specific genetic lesion responsible for this disorder is not known. Similar comments apply to many other genetic disorders. The technique of "chromosome walking" particularly suffers from the disadvantage that cloning of genomic DNA is a prerequisite. In a number of circumstances cloning may prove impossible or at least very difficult and in such situations the "chromosome walk" comes to a premature end; A. R. Wyman and K. F. Wertman, in Methods in Enzymology, Vol 152, S. L. Berger and A. R. Kummel, editors, Academic Press, San Diego, 1987, 173–180. Moreover the analysis of the fragments identified as representing overlapping clones is complex in view of inter alia the number of such fragments which may be located in any one screening of the genomic library and the fact that the overlapping sequences may be in either the 5' or the 3' sense.

Chemical Genetics provides a method for the amplification of a nucleic acid fragment, comprising unknown sequence, by primer extension which method comprises cleaving a target nucleic acid to obtain target nucleic acid fragments, one of said fragments containing an initiating priming region of known nucleotide sequence for hybridisation with an initiating primer, preparing target nucleic acid fragment/vectorette units from the target nucleic acid fragments by ligation each unit having a vectorette priming region of known sequence for hybridisation with a vectorette primer, and treating the target nucleic acid fragment/vectorette units, together or sequentially, with appropriate (deoxy) nucleoside triphosphates and an agent for polymerisation of the nucleoside triphosphates under hybridising conditions, such that an extension product of an initiating primer is synthesised complementary to a single stranded target nucleic acid/vectorette unit having an initiating priming region to which is hybridised an initiating primer selected so as to be substantially complementary to the initiating priming region, whereas no such extension product is synthesised complementary to single stranded target nucleic acid fragment/vectorette units having no such initiating priming region.

If desired the said extension product may be subjected to amplification in the presence of a vectorette primer which is selected so as to be substantially complementary to the vectorette priming region. The target nucleic acid fragment/vectorette units are thus treated with initiating primer and, if the initiating primer extension product is to be amplified for example as described by R. K. Saiki et al, Science, 2.39, 487–491 (1987), additionally treated with vectorette primer. Where no vectorette primer is used, arithmetical or linear amplification (hereinafter referred to as linear amplification) may be achieved by hybridisation of the initiating primer to the initiating priming region followed by primer extension in the presence of appropriate (deoxy) nucleoside triphosphates and an agent for polymerisation of the nucleoside triphosphates, under hybridising conditions and denaturation. This process of priming, primer extension and denaturation may be repeated as many times as appropriate to achieve the desired level of amplification. Preferably, however, amplification is effected in the presence of both initiating and vectorette primer by the use of the polymerase chain reaction (PCR) technique. Chemical Genetics amplification products may then be sequenced for further characterisation.

Using the Chemical Genetics technique we have already obtained sequence information from the ends of YAC 23CB10, 28CA12 and 26FF3. The relevant sequence information is set out in Tables 1 and 2 hereinafter.

The yeast artificial chromosome of the present invention may also be used to prepare a cosmid, phage or plasmid DNA library. For example gel purified YAC 23CB10, 28CA12 or 26FF3, conveniently purified from a low melting point agarose gel, is restricted with, for example, 6 bp recognition sequence restriction enzymes to generate appropriately sized DNA fragments which are then cloned into plasmid, cosmid or bacteriophage vectors to generate clones corresponding to DNA from the YAC. These clones are then sequenced using methods known per se to provide additional information within the YAC. Alternatively any one of YAC 23CB10, 28CA12 and 26FF3 may be sub-cloned and YAC sub-clones identified by hybridisation with dispersed human repeats such as Alu or with purified YAC DNA. In addition, sequences contained within the YAC may be used to screen libraries constructed from partial or complete genomic DNA or from cDNA. For example, sequence data derived from vectorette analysis may be used to generate an oligonucleotide or amplification product suitable for screening a library of sequences made in plasmid, phage, cosmid or YAC vectors.

In a further approach the above cosmid, phage or plasmid library may be screened with a probe to identify a variable number of tandem repeats of a nucleotide sequence for example as hereinbefore described and in particular a dinucleotide probe such as an (AC)n oligonucleotide of for example 10 base pairs to 5 kilobases, such as up to 1, up to 2, up to 3, up to 4 or up to 5 kilobases. This will reveal polymorphisms which may be used in the methods of the present invention. Convenient oligonucleotide probes may be prepared by methods well known in the art. The invention therefore also relates to polynucleotides and polynucleotide probes capable of detecting polymorphisms as outlined above.

Thus, the above methods when applied to any one of YAC 23CB10, 28CA12 and 26FF3 allow the skilled man to directly and unambiguously ascertain all, or at least a part of the Alzheimer's disease gene and its flanking regions. Genomic and cDNA clones containing the Alzheimer's disease gene may be generated using methods well known in the art.

By using any convenient combination of the above mentioned techniques, gene sequences comprised in any one of YAC 23CB10, 28CA12 and 26FF3 may be identified and characterised. By way of example cDNA clones may be identified using nucleic acid sequences comprised in the YAC as probes, either in whole using the entire YAC or in part using fragments thereof (P. Elvin et al, Nucleic Acids Research, 18, 3913–3917, 1990).

As well as being used to identify cDNA clones, probes consisting of part or all of the sequences contained within a YAC may be used to detect gene sequences on the basis of interspecies homologies by using the probes under conditions of low stringency hybridisation with nucleic acid from different species of mammal, vertebrate or other animal. For example DNA from one or more animal species is digested with a restriction endonuclease, subjected to gel electrophoresis and blotted onto a nylon filter. The presence of sequences in the animal DNA homologous to those from specific regions of human DNA are then demonstrated by using fragments of human DNA as hybridisation probes under conditions of low stringency. In these experiments the presence of blocks of sequence conserved widely amongst unrelated species is a strong indication of the presence of gene sequences. Such an approach has been used successfully in the isolation of several genes such as the tumour suppressor gene DCC (E. R. Fearon et al, 1990, Science, 247, 49–56). Gene sequences may also be identified by searching for HTF islands as described above and in the identification of the IRP gene (X. Estivill et al, 1987, Nature, 326, 840–845). A combination of any of the above strategies can also be used, as in the identification of the cystic fibrosis gene (J. M. Rommens et al, 1989, Science, 245, 1059–1065). Preferably, once a region of genomic sequence has been identified as a region of interest, for example encoding a peptide or protein, a cDNA clone is isolated from an appropriate cDNA library by standard techniques. Northern blot, primer extension and S1 mapping analyses are amongst those techniques well known in the art that may be used to yield full length, or close to full length, mRNA sequence. This can then be searched for open reading frames and potential coding sequences. Once gene(s) have been identified, assessment of involvement or otherwise of such gene(s) in a disease state can be determined. This is conveniently effected by identifying mutated or altered forms of the gene or gene product in nucleic acid or protein derived from individuals or parts thereof with the disease, but not from normal or unaffected individuals as has been demonstrated in the study of numerous inherited disorders such as cystic fibrosis and the CFTR gene (J. R. Riordan et al, 1990, Science, 245, 1066–1073) and in acquired disease such as colorectal cancer and the p53 gene (J. J. Baker et al, 1989, Science, 244, 217–221). Predicted amino acid sequence can be derived from mRNA sequence and verified by techniques well known in the art. Nucleotide sequences encoding the gene product of interest can then readily be used to derive the encoded gene product through in vitro or in vivo expression systems. For example, DNA encoding the protein or peptide is ligated into a suitable expression vector, then inserted into cells and the gene product expressed under conditions appropriate to the expression control sequences in the vector of choice. Preferably, eukaryotic genes will be expressed in eukaryotic cells such as yeast, insect, plant or mammalian cells or in vitro using eukaryotic cell derived extracts and expression control elements appropriate for the system of choice. Prokaryotes such as *E. coli* may be used for expression of peptides and proteins and this may provide higher yields of gene product, a feature which may be of benefit for example in the production of peptides or protein for the purposes of raising antibody.

A further aspect of the present invention relates to protein, or variant forms or fragments thereof, derived from a gene, preferably the Alzheimer's disease gene, comprised in any one of YAC 23CB10, 28CA12 and 26FF3 or any corresponding RNA.

A still further aspect of the invention relates to the use of protein, or variant forms or fragments thereof, derived from a gene, preferably the Alzheimer's disease gene, comprised in any one of YAC 23CB10, 28CA12 and 26FF3, or any corresponding RNA, in the diagnosis and/or therapy of inherited or acquired disease, such as CNS disorders particularly Alzheimer's disease.

In respect of diagnostic applications the presence or absence of inherited or acquired disease alleles in a sample from an individual may be determined by reference to a particular protein or proteins, or any fragment thereof, or by reference to expression, non-expression or differential expression of a particular protein or proteins.

Detection of protein and/or its level of expression may be conveniently effected using antibodies. These are conveniently polyclonal antibodies, more conveniently monoclonal antibodies, raised for example to a polypeptide sequence coded for by at least a portion of a gene comprised in the YAC of the invention or any corresponding RNA sequence. The antibody may thus bind to the protein encoded by the gene or corresponding RNA sequence or bind to any fragment or mutated form of the protein. Variant forms of the protein common to man, such as those associated with Alzheimer's Disease may be used to generate antibodies specific for the variant form, as has been demonstrated in the case of diagnostic antibodies which will bind to paired helical filament (PHF) core protein found in the cerebrospinal fluid of Alzheimer's disease patients (WO-89/03993, Medical Research Council).

The term "antibody" as used herein includes all immunoglobulins and fragments thereof which contain recognition sites for antigenic determinants of peptides of the present invention.

Antibodies which detect Alzheimer's disease gene products whether mutant, wild type or peptide fragment(s) are believed to have significant value as a diagnostic or prognostic agent. For example such antibodies may be used to detect levels of intact, wild type or total Alzheimer's disease gene products in tissue extracts or tissue sections to determine the molecular basis of the disorder and will be useful in designing therapeutic agents, particularly if they involve the Alzheimer's disease gene or its gene product(s).

Therefore according to a further aspect of the present invention we provide the use of an antibody which identifies a protein, or a fragment thereof, derived from a gene comprised in any one of YAC 23CB10, 28CA12 and 26FF3 for the diagnosis and or therapy of inherited or acquired disease, such as Alzheimer's disease.

According to a still further aspect of the present invention we provide an antibody which identifies a protein, or a fragment thereof, derived from a gene comprised in any one of YAC 23CB10, 28CA12 and 26FF3.

It will be appreciated that sequences of biological significance, such as sequences encoding proteins, commonly exhibit a high level of evolutionary conservation to the extent that they may cross hybridise under conditions of low stringency. This feature enables equivalent genes from one species to be isolated using a nucleotide probe from a second species under appropriate hybridisation conditions. This process has already been used in a large number of instances such as the isolation of human factor VIII using sequence derived from porcine factor VIII (J. Gitschier et al, 1984, Nature, 312, 326–330; J. J. Toole et al, 1984, Nature, 312, 342–347). The advent of PCR amplification technology allows oligonucleotide primers from the gene of one species to be used to amplify sequences in a second species. This approach has been used successfully for the isolation of the human aldose reductase gene using sequence taken from the aldose reductase gene of the rat (A. Graham et al, J. Biol. Chem., 1990, 266, 6872–6877). Thus, for example it is possible to identify the genes in non-human animals, such as the mouse or rat, equivalent to the human gene(s) such as the Alzheimer's disease gene comprised in any one of YAC 23CB10, 28CA12 and 26FF3.

In a still further approach the YAC of the present invention may be used to provide transgenic species such as animals and/or humans and also human and/or animal cell lines. For example rodent or human genes may be used for transfection or transgenesis such as to insert all or a part of a gene, conveniently the Alzheimer's disease gene with or without additional sequences, into the cell such that it replicates autonomously or such that it integrates into the genome at a site other than that normally occupied by the Alzheimer's disease gene. Alternatively transfection or transgenic experiments may be performed such that the cloned gene inactivates or replaces part, or all of, one or two copies of, for example the Alzheimer's disease gene in for example rodent or human cell lines.

Homologous recombination in yeast is conveniently used for the incorporation of a selectable marker, such as neomycin resistance 'neo', into YAC SC/23CB10. This is for example either directed to the 'alu' repeated sequence elements in the human DNA part of the YAC or to the vector arm (Pavan et al., 1990, Mol. Cell. Biol., 10, 4163–4169). Alternatively, targeting, such as 'neo' targeting is to a specific region of the cloned DNA (Pachnis et al., Proc. Natl. Acad. Sci., 1990, 87, 5109–5113). Homologous recombination can also be used to manipulate and alter sequences in the human DNA part of the YAC. Following manipulation and insertion of the selectable marker, the YAC is transferred into mammalian cell lines or embryo stem (ES) cells for example by polyethylene glycol mediated spheroplast fusion (Pavan et al., 1990, Mol. Cell. Biol., 10, 4163–4169; Pachnis et al., 1990, Proc. Natl. Acad. Sci., 87, 5109–5113), calcium phosphate co-precipitation (D'Urso et al., Genomics, 7, 531–534; Wigler et al., 1979, Proc. Natl. Acad. Sci., 76, 1373–1376), electroporation (T. D. Oetschman et al, 1988, P. N. A. S. USA, 85, 8583–8587; S. C. Boggs et al, 1986, Exp. Hematol, 149, 988–944), or microinjection of the purified YAC DNA directly into ES cells. Homologous recombination in the ES cells is identified for example by screening, conveniently using the polymerase chain reaction (PCR). The desired cells are then directly injected into a suitable animal such as a mouse or a rat or similar blastocyst for the generation of transgenic animals. Purified YAC with or without selectable markers can also be injected directly into the fertilised eggs of suitable animals such as mice or rats or similar animals for the generation of transgenic animals. The YAC can also be used for the generation of transgenic cell lines using the methods described above.

Expression control elements may also be used in transfection or transgenesis to place nucleotide sequences, preferably coding sequences, under at least partial control of factors that influence expression of wild type or mutant Alzheimer's disease genes. For example in transgenesis, novel mouse or rat progeny may be developed having gene(s) of interest expressed under the control of the promoter for the Alzheimer's disease gene, thereby expressing the gene in the developmental and/or tissue specific pattern normally exhibited by mutant or wild type Alzheimer's disease genes.

Therefore according to a further aspect of the present invention we provide the use of any one of YAC 23CB10, 28CA12 and 26FF3, or any convenient fragment thereof, for example as hereinbefore described, for the preparation of a transgenic species. The YAC is conveniently microinjected into cells.

According to a still further aspect of the present invention we provide a transgenic species which comprises gene sequences acquired from a gene and/or its control elements comprised in any one of YAC 23CB10, 28CA12 and 26FF3. Convenient transgenic species include animals and/or humans and also human and/or animal cell lines.

In a further aspect the present invention provides therapeutic agents derived from a gene comprised in any one of YAC 23CB10, 28CA12 and 26FF3. Convenient therapeutic agents include retroviruses and proteins, such as antibodies and fragments thereof. The therapeutic agent will comprise appropriate compounding ingredients for administration in the required dosage.

The present invention also provides therapeutic agents prepared by the "antisense" principle (Uhlman & Peyman, Chemical Reviews, 1990, 90, 543). Gene sequences comprised in any one of YAC 23CB10, 28CA12 and 26FF3, preferably gene sequences encoding Alzheimer's disease gene(s) may create highly selective targets for therapy with antisense oligonucleotides using any convenient antisense technique known in the art such as in "Oligodeoxynucleotides: Antisense Inhibitors of Gene Expression", Ed. J. S. Cohen, CRC Publishers, 1989). It will be appreciated that many different antisense oligonucleotides may be designed within the Alzheimer's disease gene but all of these derive from nucleotide sequences comprised in any one of YAC 23CB10, 28CA12 and 26FF3.

The invention will now be illustrated but not limited with reference to the following figures, tables and examples wherein:

FIGS. 1(a) and (b) show:

a) genomic and restriction map of the D21S16 and flanking region of chromosome 21. Restriction sites indicated are: B=BssHII, F=SfiI, L=SalI, N=NotI, S=SacII. The boxes indicate genomic localisation of probes as follows: C=D21S16, D=28CA12R, E=26FF3R.

b) the YAC contig of the invention at D21S16 showing the position and orientation of each YAC as well as a composite restriction map for BssH II, SacII, Eag I, Nae I, Sfi I and Xho I. Location of the D21S16 locus is indicated. Clusters of CpG-containing restriction sites are marked by boxes; those shaded in black are also seen on one or other of the genomic restriction maps.

Figure 2:
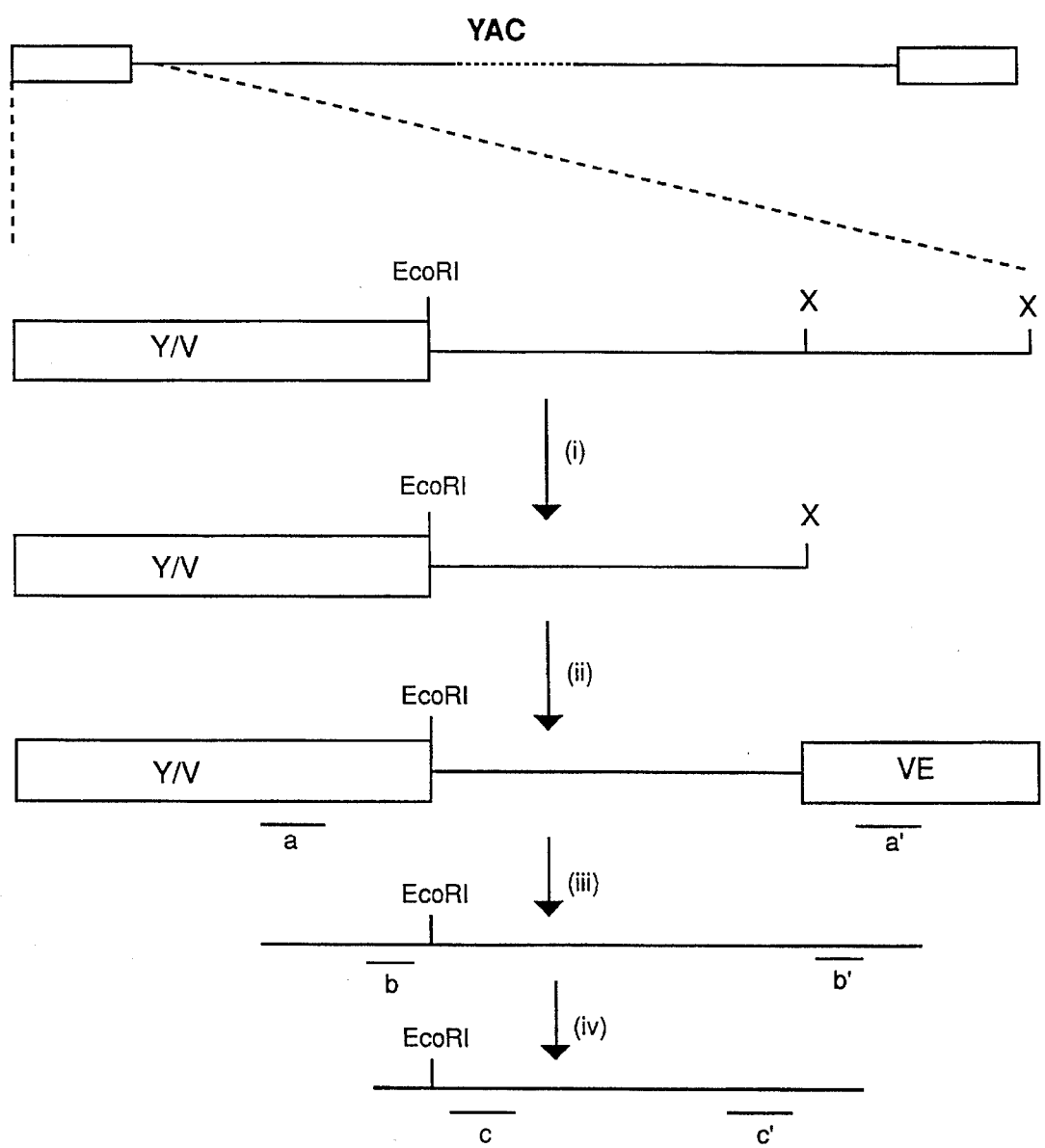

FIG. 2 shows a diagramatic representation of the Chemical Genetics vectorette technique for amplifying the ends of YAC clones. Y/V represents the YAC vector. In step (i) this is cut with restriction enzyme X. In step (ii) the vectorette, shown as VE is ligated onto the product of step (i). In step (iii) PCR primers a and a' are used to amplify the region between the YAC vector and the Vectorette. In step (iv) the procedure of step (iii) is repeated with primers b and b' and the product of this step may then be sequenced with primers c and c'.

Table 1 shows PCR primers used in library screening and YAC characterisation. N indicates that all four nucleotides are represented at this position. Approximate PCR product sizes are also listed. Sequence for primer design was obtained from direct sequencing of YAC insert-terminal PCR products except for D21S13 (P. Stinissen et al, Nucleic Acids Research, 1990, 18, 3672 and APP exon 14 (S. Yoshikai et al, Gene, 1990, 87, 257–263).

Table 2 shows nucleotide sequences determined at the ends of the YACs using Chemical Genetics techniques.

Table 3 shows nucleotide sequences identified adjacent HTF islands.

TABLE 1

| LOCATION/STS<br>OLIGONUCLEOTIDE PRIMERS<br>(5' to 3') | PCR<br>PRODUCT<br>(~bp) |
|---|---|
| APP EXON 14 | |
| CTCAGGGGACTCTTACCTTCG<br>TGTTACTCACCAAAGAGATGG | 280 |
| D21S13 | |
| ATCCATTCATCCATTCTCCC<br>CAACATCAGGTCAACCAGAG | 460 |
| 23CB10L | |
| CCATATCAGGCCCTGAATATCAGC<br>CATNAATGGCCAGATGACAGATCC | 380 |
| 23CB10R | |
| TTGGTTTCCTTNAACATCTTTGTG | 100 |

TABLE 1-continued

| LOCATION/STS OLIGONUCLEOTIDE PRIMERS (5' to 3') | PCR PRODUCT (~bp) |
|---|---|
| GCAGAAGGAGAGAAAGACCACTGG  
17BF9R | |
| CCTTATCTATATTTTCAAGTACTC  
CAGCTGGTAATATTTTGCTCTGTG  
28CA12R | 115 |
| GAATTCAGTTNNAAATATGTTGAGATTG  
CTGGCTTCAAGGACCACCTCATC  
26FF3L | 120 |
| AATTCAGTCAAGGATGACGATTGAC  
GTACACATGATTTTATTGTGTCTAC  
26FF3R | 110 |
| AGTGAATCATATAACCTAGCCATTG  
CAATTAACATTTATGAACTC | 100 |

TABLE 2

| 23CB10L | | | | | | | |
|---|---|---|---|---|---|---|---|
| GGGATATTCA  
AGCCTCCAAA | ATTCAATTGA  
TCAGCCAACT | GATTTGAGTG  
TCTGATTATT | GGGACCAAAC  
TACAGGANGG | CATATCAGGC  
CCTA | CCTGAATATC | 60  
104 |
| 23CB10R | | | | | | | |
| AAGTCTTGGT  
CCCTACTACC | TTCCTTNAAC  
CATCAGGAGT | ATCTTTGTGC  
CCAGTGGTCT | CATCTCAAAT  
TTCTCTCCTT | CTGAATATTA  
CTGCCATCA | GGTATTGTCA | 60  
109 |
| 17BF9R | | | | | | | |
| TTANCGACAG  
GTGTAGAAAT  
TANCTNTTCC | GAGACGNNTG  
CGTGTACTAT  
TTAAGGCNTT | ACCATTATAA  
ACCGATAANT  
AGANNNCTNN | NNGAGACACA  
TTACTCTTAC  
NNCG | AAGAGACACC  
GAAAACCTCA | GTTATGCATG  
TGAACTTTTA | 60  
120  
154 |
| 28CA12R | | | | | | | |
| GAATTCAGTT  
TTTCCATGAA  
AG | NNAAATATGT  
AGAGACATGG | TGAGATTGAA  
TGGGAAAAGT | GTACAAAAAC  
AAATTTGTTG | ATAGACATCT  
ATGAGGTGGT | CCAGGAGGTG  
CCTTGAAGCC | 60  
120  
122 |
| 26FF3L | | | | | | | |
| GAATTCAGTC  
TTAAAGCTAA | AAGGATGACG  
TATCTTTTAA | ATTGACAAAG  
GTATAGAAGT | GAGTCTTATC  
AGACACAATA | ATTTAAAAAA  
AAATCATGTG | TCATTTCAAA  
TAC | 60  
113 |
| 26FF3R | | | | | | | |
| GAATTCTTAA  
ACCTGGAAGC  
ATAGCT | AAGTGAATCA  
ATATTTCTGT | TATAACCTAG  
ACAAAAAATG | CCATTGTATT  
AGTTCATAAA | TCTAAGTAGT  
TGTTAATTGT | TATCCAAAAT  
TTTATTTGTA | 60  
120  
126 |

TABLE 3

| 3EH12A1 | | | | | | | |
|---|---|---|---|---|---|---|---|
| CGGGCCTGCT  
AACGGCCACC  
CCACGCGACG | TACTACAGGC  
GCGTCAAGGG  
ACGTGAAGAT | GCCCCGGCCA  
CAGCTACAAC  
C | TGGCCAGGCC  
CGGGCGGAAA | ATCGACACGG  
ACGTCTTCAA | CTGCCATCGA  
GGTCAGCAAG | 60  
120  
141 |
| 3EH12A7 | | | | | | | |
| GGTGATGCCG  
GGTGCGTGGC  
CTCCACGCGG  
GACGATGGCC  
GGCATCNCCC  
GCAGTTTGCG | TGCTCCTCCA  
CCCTTGTGCA  
CGGCGCAGGT  
GAGCAGCCCA  
GACCTTCGGC  
GCCCAGCGCA | TCATGCTGGC  
TGACATCGCA  
CTCCGTCGGT  
GGCCCTTGGC  
AGCTCATCGC  
CCGCCCGGAT | GGCATCCACG  
GGCCTGCAGC  
GAAGATGCCC  
GCTCATCTCG  
CGCTGCGCAT  
GGAGCGCGCA | GCCAGCGCGT  
GCGCGCAGGT  
TGCAGCACGC  
CGCATCAGTT  
GACATCACGC  
AA | CTTCGGCGAT  
CGGTGCCGGC  
CTGCCGCATC  
CGACAAAGCT  
ACATGGGTCA | 60  
120  
180  
240  
300  
342 |
| 3EH12A7R | | | | | | | |

TABLE 3-continued

| | | | | | | |
|---|---|---|---|---|---|---|
| GATCCACGCC | GGCACCAGCC | TCTGAATTCC | CTTAGTATTT | ATTGATCTGG | GCATGGTGAC | 60 |
| CGGCATCGAC | CTGGTGCTGG | CGCTGTCCAA | CAGCGGCGAG | GCNATGAGCT | CGCTGCGCTG | 120 |
| CTGCCGGCCA | TCAAGNCGAC | CAGGGCATAC | CCCTGGTGGC | CATGACCGGC | GGCGCGCAAT | 180 |
| CCACNCTNNC | NCGCCATGCT | GACTGGGTGC | TGGACACCGT | GTCGAGCNCG | AGGCCTGCCT | 240 |
| TTGAACCTGG | CA | | | | | 252 |
| 3EH12C6 | | | | | | |
| GATCTGTTCG | CCAATGTGCG | CGGCGCACGC | CTGCCGGCCT | GCACGCGGAA | ACCGTGCTCG | 60 |
| ATGGCCGTGG | GTTGGGCAAG | GTGCTGAAGC | GCTATCGGAT | TGCGTGAACC | ACTGCAGAGC | 120 |
| CGAGCATAGG | CTTATGGGGA | ATCCGCAGCA | ACGGGGTCAG | AGCCCTCTCC | ACAGGAGAGG | 180 |
| AATCCGACCC | CAGCGCGATG | AGCCGAGCAT | AGGCTCGTAC | GGGGAATCCG | CAGCAACGGG | 240 |
| GTCAGAGCCT | CTCCACAGGA | GAGGAATCCG | ACCCCAGCGC | GANAGGCATA | GGCTCGGCTC | 300 |
| TACGGGGAAT | CCGCAGCAAC | GGGGTCAGAG | NNCTCTCCTC | AGGAGAGGCA | TCCGACCCCG | 360 |
| GCGCCAGGGC | TTCAGCGCGC | | | | | 380 |

Construction of a Yeast Artificial Chromosome (YAC) library

High molecular weight DNA in agarose plugs was prepared from the human lymphoblastoid cell line GM1416 (48,XXXX) (National Institute of General Medical Sciences Human Genetic Mutant Cell Repository, Camden, N.J.) at a concentration of $1.5 \times 10^7$ cells/ml according to the principles of the methods of Schwartz and Cantor (1984, Cell, 37, 67–75). Details of the preparation of plugs from cell line DNA were as previously described (Anand & Southern, 1990, Gel Electrophoresis of Nucleic Acids, pp101–123, eds. D. Rickwood & B. D. Hames, IRL press, Oxford, U.K.). Individual plugs contained ~$1.5 \times 10^6$ cells and therefore had a DNA content of approximately 10 μg. For preparative fractionation, 10 complete plugs (~100 μg) were equilibrated in a 20 fold excess of 1×TE (10 mM Tris-HCl pH 7.5, 2 mM EDTA) for 16 hours at 4° C., followed by two 30 minute washes in 1×TE and a 60 minute wash in a 20× excess of EcoRI restriction buffer at 4° C. The EcoR1 buffer is 100 mM Tris-HCl pH 7.5, 50 mM NaCl, 5 mM MgCl$_2$, 100 μg/ml bovine serum albumin, 7 mM 2-mercaptoethanol or conveniently 50 mM Tris-HCl pH 7.5, 100 mM NaCl, 6 mM MgCl$_2$, 100 μg/ml gelatin, 1–2 mM Dithiothreitol. The buffer was replaced by fresh cold buffer plus EcoRI to give a final plug plus buffer volume of 3 ml and an EcoRI concentration of 5 units/ml. The plugs were kept on ice for 30 minutes with occasional mixing to allow the enzyme to equilibrate. They were then incubated at room temperature and one plug was removed every 5 minutes for 30 minutes. Incubation was continued at 37° C. and again one plug was removed every 5 minutes. Digestion was halted by dropping plugs into 40 ml cold TAE (40 mM Tris acetate pH 8.3, 2 mM EDTA) containing an additional 10 mM EDTA. This is a preferred procedure to obtain a wide range of partial digests in order to have a better representation of the human genome in the final YAC library.

Vector plasmid pYAC4 was grown and purified using standard plasmid maxi-prep protocols including caesium chloride/ethidium bromide banding (Maniatis T., Fritsch E. F., and Sambrook J., 1982, Molecular Cloning: A Laboratory Manual, Cold Spring Harbor Laboratory Press). DNA (500 μg) was digested with BamHI (200 units) and the digest was checked for completion. The salt concentration was increased, EcoRI (200 units) was added, digestion continued, and again the digest was checked for completion. The DNA was precipitated, resuspended and dephosphorylated using calf intestinal alkaline phosphatase (1 unit). The efficiency of dephosphorylation was tested by the lack of ability of the vector to self ligate but retention of it's ability to ligate to EcoRI cut DNA with phosphorylated ends.

Pulsed Field Gel Electrophoresis fractionation of EcoRI partially digested genomic DNA was performed on a "Waltzer" apparatus (Anand, R., 1986, Trends in Genetics, 2, 278–283; Southern et al, 1987, Nucleic Acids Research, 15, 5925–5943). DNA fragments >200 kb were selected and gel slices containing DNA were processed as described by Anand et al, 1989, Nucleic Acids Research, 17, 3425–3433.

Genomic DNA recovered after fractionation was concentrated under low vacuum (~300 mm Hg) to approximately 5 ml in a UH100/75 ultra thimble (vacuum dialysis membrane) using a vacuum dialysis apparatus supplied by Schleicher and Schuell. The DNA solution was then dialysed overnight in the same ultra thimble against 1 liter cold 1×TE. Dephosphorylated vector (100 μg) was added and the DNA was again concentrated to 2 ml. It was then transferred into a 15 ml sterile Falcon tube using a 1000 μl dispensing pipette with the tip cut to provide an opening of ~3 mm and 220 μl of 10×ligation buffer was added. After equilibration on ice for 1 hour, T4 DNA ligase (60 units) in 800 μl 1×ligation buffer was added with gentle movement of the dispensing tip to allow gradual dispersal. After a further one hour of equilibration on ice, the ligation mix was incubated at 12° C. overnight. This is the preferred procedure for near complete mixing of all the components in order to reduce non-contiguous insert to insert ligation events. The ligated DNA was extracted once with phenol and once with chloroform/iso-amyl alcohol using the gentle procedure described above and then transferred back to the same ultra thimble. The DNA was concentrated to 1.5 ml and transferred to a 1.5 ml Eppendorf tube again using a tip with an opening of ~3 mm. In this state the DNA could be stored at 4° C. for several months without noticeable loss in transformation efficiency.

Saccharomyces cerevisiae AB1380 (MATaΨ$^+$ ura3 trp1 ade2-1 can1-100 lys2-1 his5) cells were spheroplasted with lyticase and transformed according to published protocols (P. M. J. Burgers and K. J. Percival, 1987, Analytical Biochemistry, 163, 391–397) except that less than 2 μg ligated DNA in a volume of 30 μl was used with 700 μl spheroplasts (from 17.5 ml of yeast culture). The transformation mix was plated in agar on two 9 cm diameter plates lacking uracil and incubated at 30° C. for 48–72 hours. 100 ng uncut pYAC4 was used in a control transformation to monitor the transformation efficiency.

The primary transformation plates were used to construct a fully gridded YAC library as described previously (Anand et al., 1990, Nucleic Acids Research, 18, 1951–1956). In brief, colonies were picked from within the agar onto the surface of double selection recovery plates to form an array of 96 colonies. The plates were grown at 30° C. for three days to produce large colonies. The colonies were then innoculated into 96 well microtitre plates containing 20% glycerol in SD medium. Aliquots of each colony were innoculated onto 10×10 cm plates to form a 9×96 array (864 colonies). These master plates were grown for 24 hours at 30° C. The original recovery plates were regrown at 30° C. for 2 days when the cells were harvested to make DNA plugs for PFGE and PCR analysis. Three replica lifts were taken from the master plates on to Hybond N or similar filters and were grown overnight at 30° C. The master plates were regrown and cells harvested to make DNA plugs for PCR analysis. Two of the replicas were grown for a further 4 hours on SD agar containing 20% glycerol before storage at −70° C. Twelve slave lifts were taken from the third replica plate. The slave lifts were grown for 2 days at 30° C. prior to treatment with lyticase to spheroplast the cells. The cells were then lysed with 10% SDS, denatured with alkali, neutralised by washing with 2×SSC and DNA was fixed to the filters by baking or UV fixation. A total of 12 copies of the 40 master filters were prepared (40×864 clones).

High molecular weight yeast cell DNA was made using previously described methods (Anand et al., 1990, Nucleic Acids Research, 18, 1951–1956). Briefly, aliquots of the glycerol stocks were used to innoculate 10 ml medium (6.7 g/L Bacto yeast nitrogen base without amino acids, 20 g/L glucose, 55 mg/L adenine, 55 mg/L tyrosine, 14 g/L casamino acids) and shaken at 400 rpm overnight at 30° C. Cells were harvested, washed once in 50 mM EDTA and resuspended to 500 µl in 1M sorbitol, 20 mM EDTA, 14 mM 2-mercaptoethanol and 1 mg/ml Zymolase-20T or 20 units/ml Lyticase. Following incubation at 37° C., spheroplast formation was monitored and allowed to proceed to ~80% (~1 h). An equal volume of 1% LGT agarose in the same solution was added and the mixture was poured into a plug mould. The yeast chromosomal size marker protocol using lithium dodecyl sulphate but no protease was then followed and DNA samples were analysed on a "Waltzer" PFGE apparatus (Anand, R., 1986, Trends in Genetics, 2, 278–283; Southern et al, 1987, Nucleic Acids Research, 15, 5925–5943).

Genomic PFGE

High molecular weight DNA from the human lymphoblastoid cell line, GM1416, was prepared in LGT-agarose plugs (Schwartz and Cantor, Cell, 1984, 37, 67–75). The cells were the same culture age as those used for construction of the YAC library. The remaining protocol was essentially as described in Anand & Southern, Gel Electrophoresis of Nucleic Acids, D. Rickwood & B. Hames, IRL Press, Oxford-U.K., 1990, 101–123. In brief, each 100 ml agarose plug contained ~9 µg DNA. Prior to digestion, sufficient plugs were equilibrated with sterile TE (10 mM Tris-HCl, 1 mM diNaEDTA pH 8.0) at room temperature for 16 hours with two changes of buffer. One third of a plug was then equilibrated with 500 ml of the appropriate 1× restriction buffer (without DTT, spermidine and gelatin) on ice for two hours. Each one third plug was then transferred into 100 ml 1× restriction buffer (including 1 mM DTT, 2 mM spermidine and 100 mg/ml gelatin) and equilibriated on ice for 15' before incubation at the appropriate digestion temperature for 2–4 hours. In the case of double digests, following restriction with the first enzyme, plugs were equilibriated in the second buffer for 30' on ice then transferred to complete buffer with enzyme for equilibration and digestion. All reactions were terminated by the addition of 1 ml 0.5×TAE (1 liter comprises 2.42 g Tris base, 0.571 ml glacial acetic acid, 2 ml 0.5M diNaEDTA pH 8.0) containing an additional 10 mM diNaEDTA and kept on ice prior to loading on a pulse field gel. Each gel run also included DNA plugs that had been subjected to the same treatment without addition of enzyme in order to control for non-specific nuclease degradation.

PFGE was carried out on a Waltzer apparatus as described (Anand R., 1986, Trends in Genetics, 2, 278–283; Southern et al, 1987, Nucleic Acids Research, 15, 5925–5943). DNAs were fractionated in 1.5% agarose gels in 0.5×TAE at 150 V/300 mA with a pulse time of 65 seconds at 18° C. for ~33 hours. Under these conditions DNA fragments in the range 50–1000 kb were resolved. Lambda oligomers (Promega) and AB1380 yeast genomic DNA were used as size standards. Following electrophoresis, gels were stained, photographed and blotted with Hybond N+ using standard methods. Transferred DNA was fixed to the filter by UV crosslinking. Hybridisations were performed using our own variation of standard methods. Filters were washed down to 0.5 SSC at 65° C. before autoradiography. Filters were stripped by immersion in boiling 0.1% SDS and reexposed to film before hybridisation with subsequent probes.

Hybridisation probes used were as follows: pGSE9/D21S16 (G. D. Stewart et al., Nucleic Acids Research, 1985, 13, 4125–4132; ATCC Accession Nos. 59468/Bacteriophage, 59469/DNA), 28CA12R and 26FF3R (see Table 2). The ATCC is at 12301 Parklawn Drive, Rockville, Md. 20852, USA.

Isolation and initial characterisation of YACs

Further details relating to methods for construction and screening of a 3.5 genome equivalent YAC library of human DNA, initial characterisation of YAC clones and use of the polymerase chain reaction (PCR) with YAC DNA are described by Anand et al., Nucleic Acids Research, 1989, 17, 3425–3433; Anand et al., Nucleic Acids Research, 1990, 18, 1951–1956; and Anand et al., Genomics, 1991, 9, 124–130 and as described in our European patent application, publication no. 416801.

Restriction Mapping of YACs

DNA plugs (~3 µg) were dialysed overnight against 50 ml TE at 4° C. with gentle agitation. Plugs were then washed for a further hour with another 50 ml of TE. For each restriction enzyme, one plug was then equilibrated with 5 ml 1×digestion buffer (without DTT or gelatin) for 1 hour at 4° C. In the meantime, 100 µl aliquots of 1×reaction buffer containing different amounts of restriction enzyme (Xho I: 0.2, 4.0 & 20 units; Sfi I: 0.2, 2.0 & 20 units; BssH II: 0.16, 0.4 & 4.0 units; Nae I: 0.4, 2.0 & 20 units; Eag I: 1.0, 20 units; Not I: 2.0 & 40 units; Sac II: 2.0 & 40 units) with DTT (1 mM), Spermidine (2 mM) and gelatin (100 µg/ml) were prepared in 1.5 ml tubes on ice. One third of an appropriate, equilibrated plug (~1 µg DNA) was added to each digestion mix. All tubes were left on ice for a further 30 minutes followed by incubation at 37° C. (Xho I, Nae I, Sal I, Eag I, Not I & Sac II) or 50° C. (BssH II & Sfi I) for 1 hour (partial digests) or 2 hours (complete digests). Digests were fractionated by PFGE in 1.5% agarose gels in 0.5×TAE at 20° C. on the Waltzer PFGE apparatus using a pulse time of 5 seconds per 100 kb of YAC DNA plus 5 seconds switching time. Bacteriophage lambda concatamers and Hind III digests were used as DNA size markers. Gels were stained, photographed and blotted on to Gene Screen (Dupont) or Hybond N+ (Amersham) using standard procedures. Filters were hybridised initially with pBR322 DNA probes corresponding to each of the pYAC4 arms (Burke et al, Science, 1987, 236, 806–812), then with any available internal probes and finally with 32P-labelled lambda DNA to visualise the size markers. The resulting autoradiographs display the sizes of most partial digestion products containing each of the vector arms and any internal probes. These data were used to construct a consensus restriction map of the YAC.

The L(eft) and R(ight) arms of pYAC4 were defined as those containing the trp and ura genes respectively. Insert-terminal products (see below) were in turn designated L(eft) and R(ight) by their proximity to one or other of the pYAC4 arms. For example, 23CB10L describes the insert-terminal DNA segment adjacent to the L(eft) arm of pYAC4 in the YAC from clone SC/23CB10.

Isolation of YAC ends

The procedure for isolation of insert-terminal YAC segments using the Chemical Genetics Vectorette has been described in detail elsewhere (J. H. Riley et al, Nucleic Acids Research, 1990, 18, 2887–2890 and in our European patent application, publication no. 0416801). Briefly, the YAC-Vectorette system exploits the assymmetry of the pYAC4 vector which defines specific sequences at each end (L and R) of the artificial chromosome and the Vectorette, an oligonucleotide cassette which provides potential PCR priming sites within the terminal regions of the human DNA insert. This enables amplification of DNA between each pYAC4 arm and the Vectorette. YAC DNA, in the presence or absence of host (yeast) DNA, is restricted and Vectorette units are ligated to the exposed ends.

YAC clone DNA was digested with Hinf I, Alu I, Rsa I, Pvu II, Bgl II or EcoRV and then ligated with appropriate sticky- or blunt-ended Vectorette units (J. H. Riley et al, op cit). These "Vectorette Library" DNAs were then used as a substrate in PCR with pYAC4 L- and R-end specific and Vectorette-specific oligonucleotides to amplify insert-terminal DNA. Vectorette PCR products were sequenced directly from either end using 5' 32P-labeled primers complementary to the vector or Vectorette (FIG. 3). The resulting sequence provides potential sequence tagged sites (STS) for the YAC (Olson et al., Science, 1989, 245, 1434–1435) and can be used to design PCR primers for rescreening the YAC library. EcoRI-cut (i.e. vector-free) Vectorette PCR products can also be used as hybridisation probes.

Genomic PFGE map

Although genomic PFGE maps of the D21S13–D21S16 region were available (M. J. Owen et al., Am. J. Hum. Genet. 1990, 46, 316–322; P. Stinissen et al., Genomics, 1990, 7, 119–122) we decided to generate our own map with DNA from the cell line (GM1416) used to construct the YAC library so that any discrepancies between the YAC and genomic maps could not be attributed to different sources of genomic DNA. As the YAC walk proceeded, additional probes, generated by insert-terminus isolation, were hybridised to the same blots.

YAC contig

The YAC library was initially screened by hybridisation with the D21S16 genomic probe pGSE9. A single positive YAC clone, 23CB10 (430 kb), was isolated. This was mapped using both YAC vector arms and the pGSE9 internal probe. D21S16 was located to a 20 kb Nae I fragment ~40 kb from the R end of 23CB10. This YAC also contained a single BssHII site, ~160 kb from D21S16 but no Sac II site. Examination of our own and another genomic map of the D21S16 region (M. J. Owen et al., Am. J. Hum. Genet. 1990, 46, 316–322) allowed tentative orientation of 23CB10 on chromosome 21 with 23CB10R towards the centromere and 23CB10L towards D21S13. Even though there were several sites present in 23CB10 which were not seen on genomic maps, the BssH II and Sfi I sites immediately flanking D21S16, indicated on another genomic map (P. Stinissen et al., Genomics, 1990, 7, 119–122) could not be found. Both insert-terminal ends of 23CB10 were isolated and sequenced. PCR primers designed from these sequences were used to rescreen the YAC library.

Two further clones, 17BF9 (480 kb) and 5CE11 (240 kb) were detected with 23CB10L. These were both mapped. YAC 5CE11 was almost entirely encompassed by the Left half of 23CB10 and confirmed the map of this region. YAC 17BF9 also overlapped with most of 5EC11 but extended 240 kb towards D21S13. Only the Right hand insert-terminus, 17BF9R, was successfully isolated from this YAC; PCR with primers from 17BF9R (Table 1) detected 5CE11 and 23CB10.

Three clones 28CA12 (260 kb), 38FC5 and 31EH2 were detected in the screen with 23CB10R. The latter two were discarded in favour of 28CA12 because they contained multiple YACs. The restriction map of 28CA12 did not reveal any obvious overlap with 23CB10 but did display two groups of coincident sites for Eag I, Sac II and Nae I (FIG. 3), one of which probably corresponds to the Eag I/Sac II pair found on the centromeric side of D21S16 on one of the genomic maps (M. J. Owen et al., Am. J. Hum. Genet. 1990, 46, 316–322). Because of its repeat content and small size it was not possible to use 23CB10R in hybridisation with 28CA12 mapping blots. Both ends of 28CA12 were therefore isolated and hybridised to 23CB10 mapping blots. This allowed orientation of 28CA12 with 28CA12L placed within 23CB10, 25 kb from 23CB10R, and 28CA12R extending 235 kb towards the centromere. 28CA12R was sequenced and PCR primers used to rescreen the library. Two YACs 3EH12 (190 kb) and 26FF3 (220 kb) were isolated and mapped. 3EH12 was almost entirely encompassed by 28CA12. 26FF3 on the other hand only overlapped 28CA12 by 60 kb and extended 160 kb towards the centromere.

HTF Islands

Figure 1B:
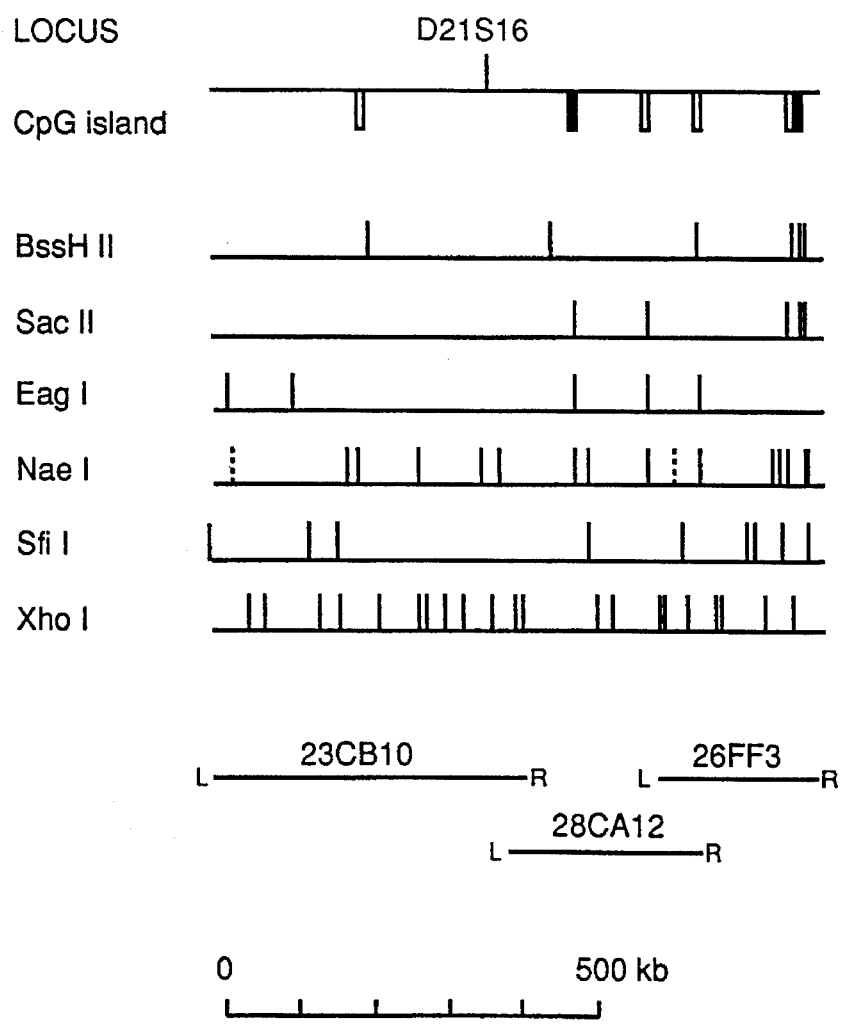

Several clusters of two or more CpG-containing rare cutter restriction sites (Bss HII, Sac II, Eag I and Nae I) were evident in the physical map of the YAC contig. Only three of these were observed on one or other of the genomic PFGE map. YAC 26FF3 is a particularly rich source of these clusters (FIG. 1).

Somatic cell hybrid (SCH) panel

DNA from a panel of five SCHs was used in PCR with pairs of primers derived from YAC ends and the control 21 q markers, D21S13 and APP exon 14 (Table 1). The panel of DNAs was designed to give a unique pattern of products with chromosome 21 markers. This assay was used to check that both ends of any YAC were derived from this chromosome. Since the a priori probability that a co-ligated YAC has both ends from chromosome 21 is <2%, this served as a reliable screen against artefacts of this kind.

Alu PCR

The method of Alu-PCR has been used since its recent introduction (D. L. Nelson et al., P. N. A. S., 1989, 86, 6686–6690) for isolation of human DNA from complex non-human backgrounds. We believed that Alu-PCR would help to determine which YACs are likely to extend a contig of YACs furthest without resort to the time-consuming step of restriction mapping and would provide evidence of non-contiguous ligation or other YAC artefacts. Using the contig described above, we have evaluated Alu-PCR as a means of "fingerprinting" overlapping YACs.

As a first step, Alu-PCR conditions were optimised. In particular, the effect of Mg2+ concentration was tested. As [Mg2+] was increased from 1 to 3 mM, both the number of visible bands and general background on EtBr stained gels was increased. In order to maximise informativity, 3 mM Mg2+ was used in all Alu-PCR reactions. Use of each Alu primer independently yielded unique patterns of products, or fingerprints, for each YAC. Use of both Alu primers in the same reaction yielded yet another fingerprint. These products were generally different from, and smaller than, those obtained with the primers used alone. This probably reflects the frequency of closely spaced Alu elements facing in the same direction and competition between individual PCR reactions in multiplex conditions. In general smaller PCR products will be made at the expense of the larger ones produced in the single primer reactions. Alu PCR fingerprints generally reflected YAC overlaps determined by PFGE mapping.

Alu PCR allows the amplification of regions flanked by Alu repeat elements within PCR distance of each other (Nelson et al., P. N. A. S., 1989, 86, 6686–6690). We used the degenerate Alu primers PDJ33 (5' GCCTCCCAAA GTGCTGGGAT TACAGG[C/T][A/G]TG AGCCA 3') and PDJ34 (5' TGAGC[C/T][G/A][A/T]GA T[C/T][G/A][C/T] [G/A]CCA[C/T]T GCACTCCAGC CTGGG 3') which correspond to positions 47–13 and 226–260 of the consensus Alu sequence and take into account the most frequent variations (W. R. Jelinek et al., Ann. Rev. Biochem., 1982, 51, 813–844; P. J. de Jong et al., Abstract 98, Human Genome I, San Diego, USA, Oct. 2–4, 1989).

PCR was carried out in a Techne PHC-1 thermal cycler in 100 μl reactions containing ~5 ng of YAC clone DNA, 10 mM Tris-HCl pH 8.5 (at room temperature), 50 mM KCl, 3.0 mM MgCl2, 0.01% gelatin, 70 pmoles of one or each Alu primer, 100 nMoles of each dNTP and 2 units Taq polymerase (Perkin-Elmer Cetus) with 50 µl mineral oil overlay. Samples were denatured at 96° C. in the thermal cycler followed by cooling to 92° C. for addition of 2 units enzyme in 2 µl 1×reaction buffer. Tubes were then subjected to 38 cycles at 92° C. for 2 minutes, 60° C. for 2 minutes and 72° C. for 2 minutes. The utmost care was taken to avoid contamination of each YAC DNA with DNA from other sources.

Identification of transcripts/coding sequences in YACs.
Cloning sequences adjacent to potential HTF islands One of the most important reasons for restriction mapping cloned DNA is the identification of all potential HTF islands. This can be done on the basis of clustering of restriction sites for enzymes which have one or more CG dinucleotides in their recognition sequence e.g. NotI, BssHII, SacII (SstII), Eag I and NaeI. These clusters of restriction sites are generally associated with gene sequences (Bird A. P. Nature 321, 209–213, 1986).

Having identified potential HTF islands, we investigated ways of specifically cloning sequences adjacent to the observed HTF islands. Clone 3EH12 was used for these experiments since this relatively small YAC comprised within the region spanned by 28CA12 had 3 potential HTF islands i.e. coincident sites for:

SacII/EagI/NaeI
SacII/EagI
BssHII/EagI/NaeI

The cloning was directed towards the SacII and BssHII sites. The 3EH12 YAC (190 kb) was purified by preparative pulsed field gel electrophoresis (PFGE) and ~100 ng DNA was digested with BssHII whilst another 100 ng was digested with SacII. The second digest for both these aliquots was with Sau3A resulting in BamHI compatible ends. The DNA was then extracted from the low gelling temperature agarose by hot phenol extractions followed by ethanol precipitation. These DNAs were ligated to BamHI/BssHII and BamHI/SacII cut Bluescript vectors (the vector was first cut with the rare cutter, gel purified and then cut with BamHI and dephosphorylated). Ligated DNA was used to transform BRL DH5alpha competent cells. The results of these transformations are shown below.

|  | Recombinant (White) | Non-Recombinant (Blue) |
| --- | --- | --- |
| BssHII/Sau3A | 300 | 180 |
| SacII/Sau3A | 64 | 56 |

Five SacII/Sau3A recombinants were analysed further. 4 of these 5 had a restriction pattern suggesting correct inserts i.e. plasmids digest with SacII but not with XbaI, a site in the discarded fragment from the plasmid polylinker. Gel analysis showed that only 3 of these 4 had detectable fragments (A1=150 bp; A7=700 bp and A8=200 bp) and further, on hybridisation to YAC mapping blots, only 2 of these 3 mapped back on to the YAC 3EH12. The fragment sizes for the two are shown below.

Seven BssHII/Sau3A recombinants were analysed further. All 7 had a restriction pattern suggesting correct inserts but gel analysis showed that only 5 of these 7 had detectable fragments (C2=350 bp; C5=150 bp; C6=500 bp; C7=270 bp and C10=290 bp). On hybridisation to YAC mapping blots, only 1 (C6) mapped back on to the YAC 3EH12. The hybridising fragment sizes are shown below.

| | Fragment sizes | | |
| --- | --- | --- | --- |
| Probe | BssHII | SacII | SfiI |
| A1 | 180kb | 6kb | 35kb |
| A7 | 180kb | 120kb | 140kb |
| C6 | 180kb | 70kb | 40kb |

This shows that the 3 clones represent the 3 different potential HTF islands identified in 3EH12. These clones were sequenced and the sequences are shown in Table 3.

The sequence data of the clone adjacent to the rare restriction site may be used to design oligonucleotides which can then be used on the YAC Vectorette libraries or on human genomic Vectorette libraries to PCR amplify DNA extending bidirectionally out from the cloned fragment. These amplification products can then be used for Southern blot analysis on "Zoo blots" which contain restricted DNA from a range of species, to study conservation of sequences as well as for Northern blot analysis to detect transcripts and on cDNA libraries to detect transcribed cDNA sequences. The analysis of cDNAs is similar to that described below in the section on screening cDNA libraries with YACs.

Screening cDNA libraries with YACs.

YACs may be used directly as hybridisation probes to screen cDNA libraries for the identification of coding sequences such as those contained in the large genomic inserts of YACs. We have previously described a reliable procedure which may be applied to any convenient YAC (Elvin et al, NAR, 18, 3913–3917, 1990, and see also Wallace et al, Science, 249, 181–186, 1990).

The YAC is first purified to homogeneity from the YAC clone. Yeast cells, preferably from a 10 ml overnight culture, are harvested and used to prepare DNA in agarose plugs (Anand and Southern, 1990, Gel Electrophoresis of Nucleic Acids. Rickwood D, Hanes B. D. (Eds), IRL Press, Oxford, p 101–123). A total of 15 plugs are loaded into a single long slot of a pulse field gel, comprising a 1.5% agarose support gel with a 1.0% Sea Plaque low gelling temperature agarose fractionating gel. Following electrophoresis the YAC is visualised by staining with ethidium bromide and excised from the gel. The low melting point agarose containing the YAC is melted at 65° C., to which an equal volume of nuclease free water is added. The mixture is then extracted twice with Phenol/TE (TE is 10 mM Tris HCl, 1 mM EDTA, pH 8.0), and the aqueous phase concentrated to approximately 100 µl by repeated extraction with butanol. Finally the YAC is precipitated from the aqueous phase, and the DNA resuspended in 10 mM Tris HCl, pH 8.0 to a final concentration of 10 ng/µl.

The YAC DNA sequences are labelled with $^{32}$P dCTP (3000 Ci mmol) by the random priming method of Feinberg and Vogelstein (Anal Biochem, 137, 1984, 266–276). In a typical labelling reaction 100 ng YAC DNA is included with 150 µCi dCTP and the labelling reaction carried out for approximately 2 hrs at 37° C., by which time approximately 70% of the radiolabelled nucleotide is incorporated into the YAC DNA.

The contribution of vector and human repeat sequences to filter hybridisation reactions is minimised by denaturing the labelled YAC, in the presence of sheared human placental DNA (Type XIII, Sigma) and sheared pBR322 DNA, by heating in a boiling water bath for 10 minutes. The DNAs are then allowed to reassociate to Cot250 in 5XSSC at 65° C., (Sealey P. G., Whittaker P. A., Southern E. M., NAR, 13, 1985, 1905–1922). Typically, reassociations are carried out in a final volume of 400 µl with a probe concentration of 0.25 µg/ml, 50 µg/ml pBR322 DNA, and sufficient human placental (driver) DNA to drive the reaction to Cot 250. It will be appreciated that the amount of driver DNA required for the reassociation reaction will be related to the size, in kilobases, of the human DNA content of the YAC, and to the time allowed for the reassociation to occur. Following the reassociation reaction the probe solution is immediately added to the hybridisation buffer at 65° C. We have achieved similar sensitivity of results following hybridisation with probe concentrations of 0.3–2.0 ng/ml probe DNA.

The probe, prepared as described, may be used to screen cDNA libraries using standard procedures familiar to those skilled in the art. Briefly, replica plaque or colony lifts are prepared on Hybond-N (Amersham) nylon membrane and prehybridised in a buffer containing, 5×SSC, 5×Denhardts, 200 ug/ml sheared salmon sperm DNA (Type lll, Sigma), 0.1% SDS, and 6% PEG 6000 for at least 6 hrs at 65° C. Hybridisation reactions are carried out in 5×SSc, 2×Denhardts, 200 µg/ml sheared salmon sperm DNA, 0.1% SDS, and 6% PEG 6000 for approximately 16 hrs at 65° C. We have also found that other pre-hybridisation and hybridisation solutions as well as extended hybridisation times work fairly efficiently. Following hybridisation the filters are washed in 2×SSC, 0.1% SDS for 20 minutes, followed by 0.5×SSC, 0.1% SDS for 20 minutes at 65° C. The filters are then wrapped in Saran Wrap and exposed to Kodak X-AR film at −70° C.

We have used the above method to generate YAC probes for screening cDNA libraries in the vector λgt11. Recombinant cDNA clones are identified from two consecutive rounds of filter hybridisation to allow the identification, and simultaneous isolation, of single positive recombinants. Before proceeding with further analysis of the cDNA clones, their homology with YAC human genomic sequences is confirmed by hybridisation. cDNAs are obtained, for example by digestion of recombinant DNA with a suitable restriction endonuclease, or by PCR amplification using oligonucleotide primers homologous to vector sequences flanking the cloning site. The cDNAs are then fractionated by electrophoresis through agarose gels and transferred to a suitable membrane by Southern blotting and finally, hybridised with the YAC probe, as described above. Only cDNAs which hybridise to the YAC are carried through further analysis.

It will be appreciated that screening a cDNA library with a large DNA probe of hundreds of kilobases may identify more than one cDNA species, representing different coding sequences cloned in a single YAC. In addition, the representation of specific cDNAs in a cDNA library may result in the selection of multiple copies of a single sequence from the library. Thus a further step in the analysis of cDNA clones is the determination of the number of unique cDNA sequences that are detected by the YAC probe. This may be conveniently carried out by cross-hybridisation, using individual YAC-positive cDNA clones as probes hybridised to Southern blots representing all of the cDNAs selected by the two rounds of YAC screening.

A final test for the origin of the cDNA clones within the genomic DNA comprising the YAC, is the localisation of the cDNA to a specific region of the cloned genomic DNA. This may be readily achieved by digesting the YAC with suitable restriction endonucleases, fractionating the restriction fragments by pulse field gel electrophoresis and Southern blotting. When the resultant filter is hybridised with a labelled cDNA clone, selected by the screening cascade described earlier above, a pattern of restriction fragments will be observed which may be used to localise the cDNA to a specific region of the YAC.

Furthermore cDNAs identified through the aforementioned screening process may be used as labelled probes for chromosomal in situ hybridisation, which will confirm the origin of the cDNAs to a known chromosomal map location. In this way the cDNA probes may also be used to specify, or confirm, the chromosomal location of the genomic sequences cloned in the YAC.

cDNAs isolated from YACs known to encompass a specific disease associated locus may also be used as hybridisation probes to provide clues as to the relative importance of homologous genes in the pathology of the disease, or provide the identity of the disease related gene. For example, many genes exhibit evolutionary conservation of DNA sequence, which may be indicative of the relative biological importance of the gene product. Thus the cDNAs may be used as hybridisation probes to demonstrate cross-hybridisation of the cDNA to the DNAs of other species. This may be conveniently performed by digesting the DNA from several species with a suitable restriction endonuclease, fractionating the resultant fragments on agarose gels followed by Southern blotting and hybridisation with a cDNA probe.

In a similar manner the cDNA may be used as a hybridisation probe in for example, Northern blot analysis, to examine tissue specific gene expression. Differences in abundance, or size, of the homologous transcript(s) in normal and disease-associated tissue may be a reflection of the role of the gene in the disease process. Other methodologies known to those skilled in the art, such as the RNAse protection assay, may be required to demonstrate changes in abundance of low abundance mRNAs. The use of the cDNA as a probe to screen a panel of DNAs from normal and diseased patients will detect any gross deletions or rearrangements at the genomic level that may be responsible for the development of the disease phenotype.

Northern blot analysis

Northern blot analysis, using hybridisation probes which may be either intact YACs, or suitable restriction fragments derived therefrom, may also be used to demonstrate the presence of coding sequences with the cloned genomic DNA. For the purpose of Northern blot analysis, any established procedure for the isolation of relatively undegraded total RNA may be used. In our laboratory total RNA was isolated from frozen tissue specimens, or from cell pellets, by a modification of the method of Chirgwin et al (J. M. Chirgwin, A. E. Przybyla, R. J. MacDonald, W. J. Rutter, Biochemistry, 1979, 18, 5294–5299), as described by P. Elvin et al, British J. Cancer, 1988, 57, 36–42.

Total RNAs, ≧2–10 µg per lane, in a buffer solution containing 50% formamide and 2.2M formaldehyde were heated to 70° C. for 10 minutes, chilled on ice, and electrophoretically fractionated on 1% agarose-formaldehyde gels. Northern blotting onto Hybond N membranes (Amersham) is performed according to the manufacturers instructions.

Further hybridisation using labelled YAC probes was carried out essentially as has already been described for the preparation and use of YAC probes to screen cDNA libraries.

Through the choice of suitable RNA samples, Northern blot analysis using YAC probes allows the assessment of tissue specific gene expression, the relative abundance of expressed sequences in different RNA samples, and the alteration of transcript size in a particular tissue or disease state.

Southern blot analysis

The use of intact YACs as hybridisation probes may be further applied to Southern blot analysis of genomic DNAs. Human genomic DNAs, digested with various restriction enzymes, are fractionated on agarose gels and transferred to a suitable membrane by a modification of the method of Southern E. M., J. Mol. Biol, 98, 503–517, 1975. Further hybridisation using YAC probes is carried out essentially as has been described for the use of YAC probes in the screening of cDNA libraries and in Northern blot analysis.

Restriction enzyme digested DNAs applied to the gels may be obtained from single individuals, or may represent pools of restriction enzyme digested DNAs from individuals sharing a particular phenotype, for example a disease phenotype. Restriction fragments identified with the YAC probe may be specific to an individual or a pool of individuals, and thus allow the identification of polymorphic restriction fragments associated with a particular phenotype.

Restriction enzyme digested DNAs applied to the gels may also be obtained from individuals of unrelated species. Hybridisation of YAC probes to the resultant Southern blot, or "Zoo blots", may demonstrate cross-hybridsation of the YAC to homologous conserved DNA sequences in several species. Since many genes exhibit an evolutionary conservation of sequence, the detection of such homologous restriction fragments may be evidence that the genomic DNA cloned in the YAC contains coding sequence(s).

I claim:

1. A method for the detection of one or more Alzheimer's disease alleles in sample nucleic acid from an individual which method comprises contacting sample nucleic acid with at least one polynucleotide probe or primer for a diagnostic locus in a gene in one of YAC 23CB10, 28CA12 and 26FF3 under selective hybridization and/or primer extension conditions at said diagnostic locus, whereby said probe or primer detects by hybridization to the alleles of said locus, which are one or more Alzheimer's disease alleles.

2. A method for the detection of one or more Alzheimer's disease alleles in sample nucleic acid from an individual which method comprises contacting sample nucleic acid from the individual and at least one or more genetically related individuals with at least one polynucleotide probe or primer for a diagnostic allele of a genetic locus in one of YAC 23CB10, 28CA12 and 26FF3 under selective hybridization and/or primer extension conditions at said diagnostic allele and detecting by selective hybridization and/or primer extension whether said diagnostic allele has been inherited from a member of the individual's family by the presence of the detected Alzheimer's disease allele in sample nucleic acid from the individual under test.

3. A method as claimed in claim 1 or 2 for the detection of pre-senile (<65 years) Alzheimer's disease.

4. A method as claimed in claim 1 or 2 wherein selective hybridization and/or primer extension is determined at a genetic locus of in a nucleic acid restriction fragment to which a polynucleotide or its complement independently selected from any one of selectively hybridizes.

hybridization and/or primer extension is determined at a genetic locus of a nucleic acid fragment to which a polynucleotide or its complement independently selected from any one of selectively hybridizes.

| | | | | | | |
|---|---|---|---|---|---|---|
| (a) | | | | | | |
| GGGATATTCA | ATTCAATTGA | GATTTGAGTG | GGGACCAAAC | CATATCAGGC | CCTGAATATC | 60 |
| AGCCTCCAAA | TCAGCCAACT | TCTGATTATT | TACAGGANGG | CCTA | | 104 |
| (SEQ ID NO: 28) | | | | | | |
| (b) | | | | | | |
| AAGTCTTGGT | TTCCTTNAAC | ATCTTTGTGC | CATCTCAAAT | CTGAATATTA | GGTATTGTCA | 60 |
| CCCTACTACC | CATCAGGAGT | CCAGTGGTCT | TTCTCTCCTT | CTGCCATCA | | 109 |
| (SEQ ID NO. 29) | | | | | | |
| (c) | | | | | | |
| TTANCGACAG | GAGACGNNTG | ACCATTATAA | NNGAGACACA | AAGAGACACC | GTTATGCATG | 60 |
| GTGTAGAAAT | CGTGTACTAT | ACCGATAANT | TTACTCTTAC | GAAAACCTCA | TGAACTTTTA | 120 |
| TANCTNTTCC | TTAAGGCNTT | AGANNNCTNN | NNCG | | | 154 |
| (SEQ ID NO. 30) | | | | | | |
| (d) | | | | | | |
| GAATTCAGTT | NNAAATATGT | TGAGATTGAA | GTACAAAAAC | ATAGACATCT | CCAGGAGGTG | 60 |
| TTTCCATGAA | AGAGACATGG | TGGGAAAAGT | AAATTTGTTG | ATGAGGTGGT | CCTTGAAGCC | 120 |
| AG | | | | | | 122 |
| (SEQ ID NO. 31) | | | | | | |
| (e) | | | | | | |
| GAATTCAGTC | AAGGATGACG | ATTGACAAAG | GAGTCTTATC | ATTTAAAAAA | TCATTTCAAA | 60 |
| TTAAAGCTAA | TATCTTTTAA | GTATAGAAGT | AGACACAATA | AAATCATGTG | TAC | 113 |
| (SEQ ID NO. 32) | | | | | | |
| (f) | | | | | | |
| GAATTCTTAA | AAGTGAATCA | TATAACCTAG | CCATTGTATT | TCTAAGTAGT | TATCCAAAAT | 60 |
| ACCTGGAAGC | ATATTTCTGT | ACAAAAAATG | AGTTCATAAA | TGTTATTGT | TTTATTTGTA | 120 |
| ATAGCT | | | | | | 126 |
| (SEQ ID NO. 33) | | | | | | |

5. A method as claimed in claim 1 or 2 wherein selective

| | | | | | | |
|---|---|---|---|---|---|---|
| (i) | | | | | | |
| CGGGCCTGCT | TACTACAGGC | GCCCCGGCCA | TGGCCAGGCC | ATCGACACGG | CTGCCATCGA | 60 |
| AACGGCCACC | GCGTCAAGGG | CAGCTACAAC | CGGGCGGAAA | ACGTCTTCAA | GGTCAGCAAG | 120 |
| CCACGCGACG | ACGTGAAGAT | C | | | | 141 |
| (SEQ ID NO. 34) | | | | | | |
| (ii) | | | | | | |
| GGTGATGCCG | TGCTCCTCCA | TCATGCTGGC | GGCATCCACG | GCCAGCGCGT | CTTCGGCGAT | 60 |
| GGTGCGTGGC | CCCTTGTGCA | TGACATCGCC | GGCCTGCAGC | GCGCGCAGGT | CGGTGCCGGC | 120 |
| CTCCACGCGG | CGGCGCAGGT | CTCCGTCGGT | GAAGATGCCC | TGCAGCACGC | CTGCCGCATC | 150 |
| GACGATGGCC | GAGCAGCCCA | GGCCCTTGGC | GCTCATCTCG | CGCATCAGTT | CGACAAAGCT | 240 |
| GGCATCNCCC | GACCTTCGGC | AGCTCATCGC | CGCTGCGCAT | GACATCACGC | ACATGGGTCA | 300 |
| GCAGTTTGCG | GCCCAGCGCA | CCGCCCGGAT | GGAGCGCGCA | AA | | 342 |
| (SEQ ID NO. 35) | | | | | | |
| (iii) | | | | | | |
| GATCCACGCC | GGCACCAGCC | TCTGAATTCC | CTTAGTATTT | ATTGATCTGG | GCATGGTGAC | 60 |
| CGGCATCGAC | CTGGTGCTGG | CGCTGTCCAA | CAGCGGCGAG | GCNATGAGCT | CGCTGCGCTG | 120 |
| CTGCCGGCCA | TCAAGNCGAC | CAGGGCATAC | CCCTGGTGGC | CATGACCGGC | GGCGCGCAAT | 180 |
| CCACNCTNNC | NGCCATGCT | GACTGGGTGC | TGGACACCGT | GTCGAGCNCG | AGGCCTGCCT | 240 |
| TTGAACCTGG | CA | | | | | 252 |
| (SEQ ID NO: 36) | | | | | | |
| or (iv) | | | | | | |
| GATCTGTTCG | CCAATGTGCG | CGGCGCACGC | CTGCCGGCCT | GCACGCGGAA | ACCGTGCTCG | 60 |
| ATGGCCGTGG | GTTGGGCAAG | GTGCTGAAGC | GCTATCGGAT | TGCGTGAACC | ACTGCAGAGC | 120 |
| CGAGCATAGG | CTTATGGGGA | ATCCGCAGCA | ACGGGGTCAG | AGCCCTCTCC | ACAGGAGAGG | 180 |
| AATCCGACCC | CAGCGCGATG | AGCCGAGCAT | AGGCTCGTAC | GGGGAATCCG | CAGCAACGGG | 240 |
| GTCAGAGCCT | CTCCACAGGA | GAGGAATCCG | ACCCAGCGC | GANAGGCATA | GGCTCGGCTC | 300 |
| TACGGGGAAT | CCGCAGCAAC | GGGGTCAGAG | NNCTCTCCTC | AGGAGAGGCA | TCCGACCCCG | 360 |
| GCGCCAGGGC | TTCAGCGCGC | | | | | 380 |
| (SEQ ID NO. 37) | | | | | | |

6. A diagnostic method as claimed in claim 1 or claim 2 wherein the probe or primer has a label or marker component.

7. A diagnostic kit which comprises one or more probes or primers as defined in claim 1 together with appropriate instructions for use and optionally contains a buffer, and test or control DNA.

8. A method for the detection of one or more Alzheimer's disease alleles in sample nucleic acid from an individual which method comprises contacting sample nucleic acid with at least one polynucleotide probe or primer for a diagnostic locus in a gene under selective hybridization and/or primer extension conditions at said diagnostic locus, whereby said probe or primer distinguishes alleles of said locus, by detecting said one or more Alzheimer's disease alleles by selective hybridization and/or primer extension wherein selective hybridization and/or primer extension is determined at a genetic locus in a nucleic acid restriction fragment to which a polynucleotide or its complement independently selected from any one of selectively hybridizes.

9. A method for the detection of one or more Alzheimer's disease alleles in sample nucleic acid from an individual which method comprises contacting sample nucleic acid with at least one polynucleotide probe or primer for a diagnostic locus in a gene under selective hybridization and/or primer extension conditions at said diagnostic locus, whereby said probe or primer distinguishes alleles of said locus, by detecting said one or more Alzheimer's disease alleles by selective hybridization and/or primer extension wherein selective hybridization and/or primer extension is determined at a genetic locus in a nucleic acid fragment to which a polynucleotide or its complement independently selected from any one of selectively hybridizes.

(a)
| GGGATATTCA | ATTCAATTGA | GATTTGAGTG | GGGACCAAAC | CATATCAGGC | CCTGAATATC | 60 |
| AGCCTCCAAA | TCAGCCAACT | TCTGATTATT | TACAGGANGG | CCTA | | 104 |
| (SEQ ID NO: 28) | | | | | | |

(b)
| AAGTCTTGGT | TTCCTTNAAC | ATCTTTGTGC | CATCTCAAAT | CTGAATATTA | GGTATTGTCA | 60 |
| CCCTACTACC | CATCAGGAGT | CCAGTGGTCT | TTCTCTCCTT | CTGCCATCA | | 109 |
| (SEQ ID NO: 29) | | | | | | |

(c)
| TTANCGACAG | GAGACGNNTG | ACCATTATAA | NNGAGACACA | AAGAGACACC | GTTATGCATG | 60 |
| GTGTAGAAAT | CGTGTACTAT | ACCGATAANT | TTACTCTTAC | GAAAACCTCA | TGAACTTTTA | 120 |
| TANCTNTTCC | TTAAGGCNTT | AGANNNCTNN | NNCG | | | 154 |
| (SEQ ID NO: 30) | | | | | | |

(d)
| GAATTCAGTT | NNAAATATGT | TGAGATTGAA | GTACAAAAAC | ATAGACATCT | CCAGGAGGTG | 60 |
| TTTCCATGAA | AGAGACATGG | TGGGAAAAGT | AAATTTGTTG | ATGAGGTGGT | CCTTGAAGCC | 120 |
| AG | | | | | | 122 |
| (SEQ ID NO: 31) | | | | | | |

(e)
| GAATTCAGTC | AAGGATGACG | ATTGACAAAG | GAGTCTTATC | ATTTAAAAAA | TCATTTCAAA | 60 |
| TTAAAGCTAA | TATCTTTTAA | GTATAGAAGT | AGACACAATA | AAATCATGTG | TAC | 113 |
| (SEQ ID NO. 32) | | | | | | |

(f)
| GAATTCTTAA | AAGTGAATCA | TATAACCTAG | CCATTGTATT | TCTAAGTAGT | TATCCAAAAT | 60 |
| ACCTGGAAGC | ATATTTCTGT | ACAAAAAATG | AGTTCATAAA | TGTTATTGT | TTTATTTGTA | 120 |
| ATAGCT | | | | | | 126 |
| (SEQ ID NO: 33) | | | | | | |

(i)
| CGGGCCTGCT | TACTACAGGC | GCCCCGGCCA | TGGCCAGGCC | ATCGACACGG | CTGCCATCGA | 60 |
| AACGGCCACC | GCGTCAAGGG | CAGCTACAAC | CGGGCGGAAA | ACGTCTTCAA | GGTCAGCAAG | 120 |
| CCACGCGACG | ACGTGAAGAT | C | | | | 141 |
| (SEQ ID NO: 34) | | | | | | |

(ii)
| GGTGATGCCG | TGCTCCTCCA | TCATGCTGGC | GGCATCCACG | GCCAGCGCGT | CTTCGGCGAT | 60 |
| GGTGCGTGGC | CCCTTGTGCA | TGACATCGCC | GGCCTGCAGC | GCGCGCAGGT | CGGTGCCGGC | 120 |
| CTCCACGCGG | CGGCGCAGGT | CTCCGTCGGT | GAAGATGCCC | TGCAGCACGC | CTGCCGCATC | 180 |
| GACGATGGCC | GAGCAGCCCA | GGCCCTTGGC | GCTCATCTCG | CGCATCAGTT | CGACAAAGCT | 240 |
| GGCATCNCCC | GACCTTCGGC | AGCTCATCGC | CGCTGCGCAT | GACATCACGC | ACATGGGTCA | 300 |
| GCAGTTTGCG | GCCCAGCGCA | CCGCCCGGAT | GGAGCGCGCA | AA | | 342 |
| (SEQ ID NO: 35) | | | | | | |

(iii)
| GATCCACGCC | GGCACCAGCC | TCTGAATTCC | CTTAGTATTT | ATTGATCTGG | GCATGGTGAC | 60 |
| CGGCATCGAC | CTGGTGCTGG | CGCTGTCCAA | CAGCGGCGAG | GCNATGAGCT | CGCTGCGCTG | 120 |
| CTGCCGGCCA | TCAAGNCGAC | CAGGGCATAC | CCCTGGTGGC | CATGACCGGC | GGCGCGCAAT | 180 |
| CCACNCTNNC | NCGCCATGCT | GACTGGGTGC | TGGACACCGT | GTCGAGCNCG | AGGCCTGCCT | 240 |
| TTGAACCTGG | CA | | | | | 252 |
| (SEQ ID NO: 36) | | | | | | |

-continued

| or (iv) | | | | | | | |
|---|---|---|---|---|---|---|---|
| GATCTGTTCG | CCAATGTGCG | CGGCGCACGC | CTGCCGGCCT | GCACGCGGAA | ACCGTGCTCG | | 60 |
| ATGGCCGTGG | GTTGGGCAAG | GTGCTGAAGC | GCTATCGGAT | TGCGTGAACC | ACTGCAGAGC | | 120 |
| CGAGCATAGG | CTTATGGGGA | ATCCGCAGCA | ACGGGGTCAG | AGCCCTCTCC | ACAGGAGAGG | | 180 |
| AATCCGACCC | CAGCGCGATG | AGCCGAGCAT | AGGCTCGTAC | GGGGAATCCG | CAGCAACGGG | | 240 |
| GTCAGAGCCT | CTCCACAGGA | GAGGAATCCG | ACCCCAGCGC | GANAGGCATA | GGCTCGGCTC | | 300 |
| TACGGGGAAT | CCGCAGCAAC | GGGGTCAGAG | NNCTCTCCTC | AGGAGAGGCA | TCCGACCCCG | | 360 |
| GCGCCAGGGC | TTCAGCGCGC | | | | | | 380 |
| (SEQ ID NO: 37) | | | | | | | |

10. A method for the detection of one or more Alzheimer's disease alleles in sample nucleic acid from an individual which method comprises contacting sample nucleic acid isolated from the individual and at least one or more genetically related individuals with at least one polynucleotide probe or primer for a diagnostic allele of a genetic locus under selective hybridization and/or primer extension conditions at said diagnostic allele and detecting by selective hybridization and/or primer extension whether said diagnostic allele has been inherited from a member of the individual's family by the presence of the detected Alzheimer's disease allele in sample nucleic acid from the individual under test wherein selective hybridization and/or primer extension is determined at a genetic locus comprised in a nucleic acid fragment to which a polynucleotide or its complement independently selected from any one of selectively hybridizes.

disease alleles in sample nucleic acid from an individual which method comprises contacting sample nucleic acid isolated from the individual and at least one or more genetically related individuals with at least one polynucleotide probe or primer for a diagnostic allele of a genetic locus under selective hybridization and/or primer extension conditions at said diagnostic allele and detecting by selective hybridization and/or primer extension whether said diagnostic allele has been inherited from a member of the individual's family by the presence of an Alzheimer's disease allele in sample nucleic acid from the individual under test wherein selective hybridization and/or primer extension is determined at a genetic locus comprised in a nucleic acid fragment to which a polynucleotide or its complement independently selected from any one of selectively hybridizes.

| (a) | | | | | | | |
|---|---|---|---|---|---|---|---|
| GGGATATTCA | ATTCAATTGA | GATTTGAGTG | GGGACCAAAC | CATATCAGGC | CCTGAATATC | | 60 |
| AGCCTCCAAA | TCAGCCAACT | TCTGATTATT | TACAGGANGG | CCTA | | | 104 |
| (SEQ ID NO: 28) | | | | | | | |
| (b) | | | | | | | |
| AAGTCTTGGT | TTCCTTNAAC | ATCTTTGTGC | CATCTCAAAT | CTGAATATTA | GGTATTGTCA | | 60 |
| CCCTACTACC | CATCAGGAGT | CCAGTGGTCT | TTCTCTCCTT | CTGCCATCA | | | 109 |
| (SEQ ID NO: 29) | | | | | | | |
| (c) | | | | | | | |
| TTANCGACAG | GAGACGNNTG | ACCATTATAA | NNGAGACACA | AAGAGACACC | GTTATGCATG | | 60 |
| GTGTAGAAAT | CGTGTACTAT | ACCGATAANT | TTACTCTTAC | GAAAACCTCA | TGAACTTTTA | | 120 |
| TANCTNTTCC | TTAAGGCNTT | AGANNNCTNN | NNCG | | | | 154 |
| (SEQ ID NO: 30) | | | | | | | |
| (d) | | | | | | | |
| GAATTCAGTT | NNAAATATGT | TGAGATTGAA | GTACAAAAAC | ATAGACATCT | CCAGGAGGTG | | 60 |
| TTTCCATGAA | AGAGACATGG | TGGGAAAAGT | AAATTTGTTG | ATGAGGTGGT | CCTTGAAGCC | | 120 |
| AG | | | | | | | 122 |
| (SEQ ID NO: 31) | | | | | | | |
| (e) | | | | | | | |
| GAATTCAGTC | AAGGATGACG | ATTGACAAAG | GAGTCTTATC | ATTTAAAAAA | TCATTTCAAA | | 60 |
| TTAAAGCTAA | TATCTTTTAA | GTATAGAAGT | AGACACAATA | AAATCATGTG | TAC | | 113 |
| (SEQ ID NO: 32) | | | | | | | |
| (f) | | | | | | | |
| GAATTCTTAA | AAGTGAATCA | TATAACCTAG | CCATTGTATT | TCTAAGTAGT | TATCCAAAAT | | 60 |
| ACCTGGAAGC | ATATTTCTGT | ACAAAAAATG | AGTTCATAAA | TGTTATTGT | TTTATTTGTA | | 120 |
| ATAGCT | | | | | | | 126 |
| (SEQ ID NO: 33) | | | | | | | |

11. A method for the detection of one or more Alzheimer's

| (i) | | | | | | | |
|---|---|---|---|---|---|---|---|
| CGGGCCTGCT | TACTACAGGC | GCCCCGGCCA | TGGCCAGGCC | ATCGACACGG | CTGCCATCGA | | 60 |
| AACGGCCACC | GCGTCAAGGG | CAGCTACAAC | CGGGCGGAAA | ACGTCTTCAA | GGTCAGCAAG | | 120 |
| CCACGCGACG | ACGTGAAGAT | C | | | | | 141 |
| (SEQ ID NO: 34) | | | | | | | |
| (ii) | | | | | | | |
| GGTGATGCCG | TGCTCCTCCA | TCATGCTGGC | GGCATCCACG | GCCAGCGCGT | CTTCGGCGAT | | 60 |
| GGTGCGTGGC | CCCTTGTGCA | TGACATCGCC | GGCCTGCAGC | GCGCGCAGGT | CGGTGCCGGC | | 120 |
| CTCCACGCGG | CGGCGCAGGT | CTCCGTCGGT | GAAGATGCCC | TGCAGCACGC | CTGCCGCATC | | 180 |
| GACGATGGCC | GAGCAGCCCA | GGCCCTTGGC | GCTCATCTCG | CGCATCAGTT | CGACAAAGCT | | 240 |
| GGCATCNCCC | GACCTTCGGC | AGCTCATCGC | CGCTGCGCAT | GACATCACGC | ACATGGGTCA | | 300 |

| | | | | | | |
|---|---|---|---|---|---|---|
| GCAGTTTGCG (SEQ ID NO: 35) | GCCCAGCGCA | CCGCCCGGAT | GGAGCGCGCA | AA | | 342 |
| (iii) GATCCACGCC | GGCACCAGCC | TCTGAATTCC | CTTAGTATTT | ATTGATCTGG | GCATGGTGAC | 60 |
| CGGCATCGAC | CTGGTGCTGG | CGCTGTCCAA | CAGCGGCGAG | GCNATGAGCT | CGCTGCGCTG | 120 |
| CTGCCGGCCA | TCAAGNCGAC | CAGGGCATAC | CCCTGGTGGC | CATGACCGGC | GGCGCGCAAT | 180 |
| CCACNCTNNC | NCGCCATGCT | GACTGGGTGC | TGGACACCGT | GTCGAGCNCG | AGGCCTGCCT | 240 |
| TTGAACCTGG (SEQ ID NO: 36) | CA | | | | | 252 |
| or (iv) GATCTGTTCG | CCAATGTGCG | CGGCGCACGC | CTGCCGGCCT | GCACGCGGAA | ACCGTGCTCG | 60 |
| ATGGCCGTGG | GTTGGGCAAG | GTGCTGAAGC | GCTATCGGAT | TGCGTGAACC | ACTGCAGAGC | 120 |
| CGAGCATAGG | CTTATGGGGA | ATCCGCAGCA | ACGGGGTCAG | AGCCCTCTCC | ACAGGAGAGG | 180 |
| AATCCGACCC | CAGCGCGATG | AGCCGAGCAT | AGGCTCGTAC | GGGGAATCCG | CAGCAACGGG | 240 |
| GTCAGAGCCT | CTCCACAGGA | GAGGAATCCG | ACCCCAGCGC | GANAGGCATA | GGCTCGGCTC | 300 |
| TACGGGGAAT | CCGCAGCAAC | GGGGTCAGAG | NNCTCTCCTC | AGGAGAGGCA | TCCGACCCCG | 360 |
| GCGCCAGGGC (SEQ ID NO: 37) | TTCAGCGCGC | | | | | 380 |

SEQUENCE LISTING ( 1 ) GENERAL INFORMATION:

( i i i ) NUMBER OF SEQUENCES: 37

( 2 ) INFORMATION FOR SEQ ID NO:1:

( i ) SEQUENCE CHARACTERISTICS:
        ( A ) LENGTH: 28
        ( B ) TYPE: Nucleic acid
        ( C ) STRANDEDNESS: Single
        ( D ) TOPOLOGY: Linear ( x i ) SEQUENCE DESCRIPTION: SEQ ID NO:1:

ACCCGTTCTC GGAGCACTGT CCGACCGC 28

( 2 ) INFORMATION FOR SEQ ID NO:2:

( i ) SEQUENCE CHARACTERISTICS:
        ( A ) LENGTH: 27
        ( B ) TYPE: Nucleic acid
        ( C ) STRANDEDNESS: Single
        ( D ) TOPOLOGY: Linear ( x i ) SEQUENCE DESCRIPTION: SEQ ID NO:2:

AGTCCTGCTC GCTTCGCTAC TTGGAGC 27

( 2 ) INFORMATION FOR SEQ ID NO:3:

( i ) SEQUENCE CHARACTERISTICS:
        ( A ) LENGTH: 28
        ( B ) TYPE: Nucleic acid
        ( C ) STRANDEDNESS: Single
        ( D ) TOPOLOGY: Linear ( x i ) SEQUENCE DESCRIPTION: SEQ ID NO:3:

GTGTTATGTA GTATACTCTT TCTTCAAC 28

( 2 ) INFORMATION FOR SEQ ID NO:4:

( i ) SEQUENCE CHARACTERISTICS:
        ( A ) LENGTH: 28
        ( B ) TYPE: Nucleic acid
        ( C ) STRANDEDNESS: Single
        ( D ) TOPOLOGY: Linear ( x i ) SEQUENCE DESCRIPTION: SEQ ID NO:4:

CTTCAACAAT TAAATACTCT CGGTAGCC 28

( 2 ) INFORMATION FOR SEQ ID NO:5:

( i ) SEQUENCE CHARACTERISTICS:
        ( A ) LENGTH: 18
        ( B ) TYPE: Nucleic acid
        ( C ) STRANDEDNESS: Single
        ( D ) TOPOLOGY: Linear ( x i ) SEQUENCE DESCRIPTION: SEQ ID NO:5:

GTTGGTTTAA GGCGCAAG 18

(2) INFORMATION FOR SEQ ID NO:6:

(i) SEQUENCE CHARACTERISTICS:
        (A) LENGTH: 27
        (B) TYPE: Nucleic acid
        (C) STRANDEDNESS: Single
        (D) TOPOLOGY: Linear (xi) SEQUENCE DESCRIPTION: SEQ ID NO:6:

ATAGGCGCCA GCAACCGCAC CTGTGGC        27

(2) INFORMATION FOR SEQ ID NO:7:

(i) SEQUENCE CHARACTERISTICS:
        (A) LENGTH: 27
        (B) TYPE: Nucleic acid
        (C) STRANDEDNESS: Single
        (D) TOPOLOGY: Linear (xi) SEQUENCE DESCRIPTION: SEQ ID NO:7:

ACCTGTGGCG CCGGTGATGC CGGCCAC        27

(2) INFORMATION FOR SEQ ID NO:8:

(i) SEQUENCE CHARACTERISTICS:
        (A) LENGTH: 28
        (B) TYPE: Nucleic acid
        (C) STRANDEDNESS: Single
        (D) TOPOLOGY: Linear (xi) SEQUENCE DESCRIPTION: SEQ ID NO:8:

CTTGCAAGTC TGGGAAGTGA ATGGAGAC        28

(2) INFORMATION FOR SEQ ID NO:9:

(i) SEQUENCE CHARACTERISTICS:
        (A) LENGTH: 20
        (B) TYPE: Nucleic acid
        (C) STRANDEDNESS: Single
        (D) TOPOLOGY: Linear (xi) SEQUENCE DESCRIPTION: SEQ ID NO:9:

GTCGAACGCC CGATCTCAAG        20

(2) INFORMATION FOR SEQ ID NO:10:

(i) SEQUENCE CHARACTERISTICS:
        (A) LENGTH: 35
        (B) TYPE: Nucleic acid
        (C) STRANDEDNESS: Single
        (D) TOPOLOGY: Linear (xi) SEQUENCE DESCRIPTION: SEQ ID NO:10:

GCCTCCCAAA GTGCTGGGAT TACAGGYRTG AGCCA        35

(2) INFORMATION FOR SEQ ID NO:11:

(i) SEQUENCE CHARACTERISTICS:
        (A) LENGTH: 35
        (B) TYPE: Nucleic acid
        (C) STRANDEDNESS: Single
        (D) TOPOLOGY: Linear (xi) SEQUENCE DESCRIPTION: SEQ ID NO:11:

TGAGCYRWGA TYRYRCCAYT GCACTCCAGC CTGGG        35

( 2 ) INFORMATION FOR SEQ ID NO:12:

( i ) SEQUENCE CHARACTERISTICS:
        ( A ) LENGTH: 21
        ( B ) TYPE: Nucleic acid
        ( C ) STRANDEDNESS: Single
        ( D ) TOPOLOGY: Linear ( x i ) SEQUENCE DESCRIPTION: SEQ ID NO:12:

CTCAGGGGAC TCTTACCTTC G            21

( 2 ) INFORMATION FOR SEQ ID NO:13:

( i ) SEQUENCE CHARACTERISTICS:
        ( A ) LENGTH: 21
        ( B ) TYPE: Nucleic acid
        ( C ) STRANDEDNESS: Single
        ( D ) TOPOLOGY: Linear ( x i ) SEQUENCE DESCRIPTION: SEQ ID NO:13:

TGTTACTCAC CAAAGAGATG G            21

( 2 ) INFORMATION FOR SEQ ID NO:14:

( i ) SEQUENCE CHARACTERISTICS:
        ( A ) LENGTH: 20
        ( B ) TYPE: Nucleic acid
        ( C ) STRANDEDNESS: Single
        ( D ) TOPOLOGY: Linear ( x i ) SEQUENCE DESCRIPTION: SEQ ID NO:14:

ATCCATTCAT CCATTCTCCC             20

( 2 ) INFORMATION FOR SEQ ID NO:15:

( i ) SEQUENCE CHARACTERISTICS:
        ( A ) LENGTH: 20
        ( B ) TYPE: Nucleic acid
        ( C ) STRANDEDNESS: Single
        ( D ) TOPOLOGY: Linear ( x i ) SEQUENCE DESCRIPTION: SEQ ID NO:15:

CAACATCAGG TCAACCAGAG            20

( 2 ) INFORMATION FOR SEQ ID NO:16:

( i ) SEQUENCE CHARACTERISTICS:
        ( A ) LENGTH: 24
        ( B ) TYPE: Nucleic acid
        ( C ) STRANDEDNESS: Single
        ( D ) TOPOLOGY: Linear ( x i ) SEQUENCE DESCRIPTION: SEQ ID NO:16:

CCATATCAGG CCCTGAATAT CAGC         24

( 2 ) INFORMATION FOR SEQ ID NO:17:

( i ) SEQUENCE CHARACTERISTICS:
        ( A ) LENGTH: 24
        ( B ) TYPE: Nucleic acid
        ( C ) STRANDEDNESS: Single
        ( D ) TOPOLOGY: Linear ( x i ) SEQUENCE DESCRIPTION: SEQ ID NO:17:

CATNAATGGC CAGATGACAG ATCC         24

( 2 ) INFORMATION FOR SEQ ID NO:18:

( i ) SEQUENCE CHARACTERISTICS:
    ( A ) LENGTH: 24
    ( B ) TYPE: Nucleic acid
    ( C ) STRANDEDNESS: Single
    ( D ) TOPOLOGY: Linear ( x i ) SEQUENCE DESCRIPTION: SEQ ID NO:18:

TTGGTTTCCT TNAACATCTT TGTG                                                          24

( 2 ) INFORMATION FOR SEQ ID NO:19:

( i ) SEQUENCE CHARACTERISTICS:
        ( A ) LENGTH: 24
        ( B ) TYPE: Nucleic acid
        ( C ) STRANDEDNESS: Single
        ( D ) TOPOLOGY: Linear ( x i ) SEQUENCE DESCRIPTION: SEQ ID NO:19:

GCAGAAGGAG AGAAAGACCA CTGG                                                          24

( 2 ) INFORMATION FOR SEQ ID NO:20:

( i ) SEQUENCE CHARACTERISTICS:
        ( A ) LENGTH: 24
        ( B ) TYPE: Nucleic acid
        ( C ) STRANDEDNESS: Single
        ( D ) TOPOLOGY: Linear ( x i ) SEQUENCE DESCRIPTION: SEQ ID NO:20:

CCTTATCTAT ATTTTCAAGT ACTC                                                          24

( 2 ) INFORMATION FOR SEQ ID NO:21:

( i ) SEQUENCE CHARACTERISTICS:
        ( A ) LENGTH: 24
        ( B ) TYPE: Nucleic acid
        ( C ) STRANDEDNESS: Single
        ( D ) TOPOLOGY: Linear ( x i ) SEQUENCE DESCRIPTION: SEQ ID NO:21:

CAGCTGGTAA TATTTTGCTC TGTG                                                          24

( 2 ) INFORMATION FOR SEQ ID NO:22:

( i ) SEQUENCE CHARACTERISTICS:
        ( A ) LENGTH: 28
        ( B ) TYPE: Nucleic acid
        ( C ) STRANDEDNESS: Single
        ( D ) TOPOLOGY: Linear ( x i ) SEQUENCE DESCRIPTION: SEQ ID NO:22:

GAATTCAGTT NNAAATATGT TGAGATTG                                                      28

( 2 ) INFORMATION FOR SEQ ID NO:23:

( i ) SEQUENCE CHARACTERISTICS:
        ( A ) LENGTH: 23
        ( B ) TYPE: Nucleic acid
        ( C ) STRANDEDNESS: Single
        ( D ) TOPOLOGY: Linear ( x i ) SEQUENCE DESCRIPTION: SEQ ID NO:23:

CTGGCTTCAA GGACCACCTC ATC                                                           23

( 2 ) INFORMATION FOR SEQ ID NO:24:

( i ) SEQUENCE CHARACTERISTICS:
        ( A ) LENGTH: 25

( B ) TYPE: Nucleic acid
            ( C ) STRANDEDNESS: Single
            ( D ) TOPOLOGY: Linear ( x i ) SEQUENCE DESCRIPTION: SEQ ID NO:24:

AATTCAGTCA AGGATGACGA TTGAC                           25

( 2 ) INFORMATION FOR SEQ ID NO:25:

( i ) SEQUENCE CHARACTERISTICS:
            ( A ) LENGTH: 25
            ( B ) TYPE: Nucleic acid
            ( C ) STRANDEDNESS: Single
            ( D ) TOPOLOGY: Linear ( x i ) SEQUENCE DESCRIPTION: SEQ ID NO:25:

GTACACATGA TTTTATTGTG TCTAC                           25

( 2 ) INFORMATION FOR SEQ ID NO:26:

( i ) SEQUENCE CHARACTERISTICS:
            ( A ) LENGTH: 25
            ( B ) TYPE: Nucleic acid
            ( C ) STRANDEDNESS: Single
            ( D ) TOPOLOGY: Linear ( x i ) SEQUENCE DESCRIPTION: SEQ ID NO:26:

AGTGAATCAT ATAACCTAGC CATTG                           25

( 2 ) INFORMATION FOR SEQ ID NO:27:

( i ) SEQUENCE CHARACTERISTICS:
            ( A ) LENGTH: 20
            ( B ) TYPE: Nucleic acid
            ( C ) STRANDEDNESS: Single
            ( D ) TOPOLOGY: Linear ( x i ) SEQUENCE DESCRIPTION: SEQ ID NO:27:

CAATTAACAT TTATGAACTC                                 20

( 2 ) INFORMATION FOR SEQ ID NO:28:

( i ) SEQUENCE CHARACTERISTICS:
            ( A ) LENGTH: 104
            ( B ) TYPE: Nucleic acid
            ( C ) STRANDEDNESS: Single
            ( D ) TOPOLOGY: Linear ( x i ) SEQUENCE DESCRIPTION: SEQ ID NO:28:

GGGATATTCA ATTCAATTGA GATTTGAGTG GGGACCAAAC CATATCAGGC CTGAATATC   60

AGCCTCCAAA TCAGCCAACT TCTGATTATT TACAGGANGG CCTA                 104

( 2 ) INFORMATION FOR SEQ ID NO:29:

( i ) SEQUENCE CHARACTERISTICS:
            ( A ) LENGTH: 109
            ( B ) TYPE: Nucleic acid
            ( C ) STRANDEDNESS: Single
            ( D ) TOPOLOGY: Linear ( x i ) SEQUENCE DESCRIPTION: SEQ ID NO:29:

AAGTCTTGGT TTCCTTNAAC ATCTTTGTGC CATCTCAAAT CTGAATATTA GGTATTGTCA   60

CCCTACTACC CATCAGGAGT CCAGTGGTCT TTCTCTCCTT CTGCCATCA              109

( 2 ) INFORMATION FOR SEQ ID NO:30:

( i ) SEQUENCE CHARACTERISTICS:
  ( A ) LENGTH: 154
  ( B ) TYPE: Nucleic acid
  ( C ) STRANDEDNESS: Single
  ( D ) TOPOLOGY: Linear ( x i ) SEQUENCE DESCRIPTION: SEQ ID NO:30:

```
TTANCGACAG GAGACGNNTG ACCATTATAA NNGAGACACA AAGAGACACC GTTATGCATG    60
GTGTAGAAAT CGTGTACTAT ACCGATAANT TTACTCTTAC GAAAACCTCA TGAACTTTTA   120
TANCTNTTCC TTAAGGCNTT AGANNCTNN NNCG                                154
```

( 2 ) INFORMATION FOR SEQ ID NO:31:

( i ) SEQUENCE CHARACTERISTICS:
    ( A ) LENGTH: 122
    ( B ) TYPE: Nucleic acid
    ( C ) STRANDEDNESS: Single
    ( D ) TOPOLOGY: Linear ( x i ) SEQUENCE DESCRIPTION: SEQ ID NO:31:

```
GAATTCAGTT NNAAATATGT TGAGATTGAA GTACAAAAAC ATAGACATCT CCAGGAGGTG    60
TTTCCATGAA AGAGACATGG TGGGAAAAGT AAATTTGTTG ATGAGGTGGT CCTTGAAGCC   120
AG                                                                  122
```

( 2 ) INFORMATION FOR SEQ ID NO:32:

( i ) SEQUENCE CHARACTERISTICS:
    ( A ) LENGTH: 113
    ( B ) TYPE: Nucleic acid
    ( C ) STRANDEDNESS: Single
    ( D ) TOPOLOGY: Linear ( x i ) SEQUENCE DESCRIPTION: SEQ ID NO:32:

```
GAATTCAGTC AAGGATGACG ATTGACAAAG GAGTCTTATC ATTTAAAAAA TCATTTCAAA    60
TTAAAGCTAA TATCTTTTAA GTATAGAAGT AGACACAATA AAATCATGTG TAC          113
```

( 2 ) INFORMATION FOR SEQ ID NO:33:

( i ) SEQUENCE CHARACTERISTICS:
    ( A ) LENGTH: 126
    ( B ) TYPE: Nucleic acid
    ( C ) STRANDEDNESS: Single
    ( D ) TOPOLOGY: Linear ( x i ) SEQUENCE DESCRIPTION: SEQ ID NO:33:

```
GAATTCTTAA AAGTGAATCA TATAACCTAG CCATTGTATT TCTAAGTAGT TATCCAAAAT    60
ACCTGGAAGC ATATTTCTGT ACAAAAAATG AGTTCATAAA TGTTAATTGT TTTATTTGTA   120
ATAGCT                                                              126
```

( 2 ) INFORMATION FOR SEQ ID NO:34:

( i ) SEQUENCE CHARACTERISTICS:
    ( A ) LENGTH: 141
    ( B ) TYPE: Nucleic acid
    ( C ) STRANDEDNESS: Single
    ( D ) TOPOLOGY: Linear ( x i ) SEQUENCE DESCRIPTION: SEQ ID NO:34:

```
CGGGCCTGCT TACTACAGGC GCCCCGGCCA TGGCCAGGCC ATCGACACGG CTGCCATCGA    60
AACGGCCACC GCGTCAAGGG CAGCTACAAC CGGGCGGAAA ACGTCTTCAA GGTCAGCAAG   120
CCACGCGACG ACGTGAAGAT C                                             141
```

(2) INFORMATION FOR SEQ ID NO:35:

(i) SEQUENCE CHARACTERISTICS:
        (A) LENGTH: 342
        (B) TYPE: Nucleic acid
        (C) STRANDEDNESS: Single
        (D) TOPOLOGY: Linear (xi) SEQUENCE DESCRIPTION: SEQ ID NO:35:

```
GGTGATGCCG  TGCTCCTCCA  TCATGCTGGC  GGCATCCACG  GCCAGCGCGT  CTTCGGCGAT   60
GGTGCGTGGC  CCCTTGTGCA  TGACATCGCC  GGCCTGCAGC  GCGCGCAGGT  CGGTGCCGGC  120
CTCCACGCGG  CGGCGCAGGT  CTCCGTCGGT  GAAGATGCCC  TGCAGCACGC  CTGCCGCATC  180
GACGATGGCC  GAGCAGCCCA  GGCCCTTGGC  GCTCATCTCG  CGCATCAGTT  CGACAAAGCT  240
GGCATCNCCC  GACCTTCGGC  AGCTCATCGC  CGCTGCGCAT  GACATCACGC  ACATGGGTCA  300
GCAGTTTGCG  GCCCAGCGCA  CCGCCCGGAT  GGAGCGCGCA  AA                      342
```

(2) INFORMATION FOR SEQ ID NO:36:

(i) SEQUENCE CHARACTERISTICS:
        (A) LENGTH: 252
        (B) TYPE: Nucleic acid
        (C) STRANDEDNESS: Single
        (D) TOPOLOGY: Linear (xi) SEQUENCE DESCRIPTION: SEQ ID NO:36:

```
GATCCACGCC  GGCACCAGCC  TCTGAATTCC  CTTAGTATTT  ATTGATCTGG  GCATGGTGAC   60
CGGCATCGAC  CTGGTGCTGG  CGCTGTCCAA  CAGCGGCGAG  GCNATGAGCT  CGCTGCGCTG  120
CTGCCGGCCA  TCAAGNCGAC  CAGGGCATAC  CCCTGGTGGC  CATGACCGGC  GGCGCGCAAT  180
CCACNCTNNC  NCGCCATGCT  GACTGGGTGC  TGGACACCGT  GTCGAGCNCG  AGGCCTGCCT  240
TTGAACCTGG  CA                                                          252
```

(2) INFORMATION FOR SEQ ID NO:37:

(i) SEQUENCE CHARACTERISTICS:
        (A) LENGTH: 380
        (B) TYPE: Nucleic acid
        (C) STRANDEDNESS: Single
        (D) TOPOLOGY: Linear (xi) SEQUENCE DESCRIPTION: SEQ ID NO:37:

```
GATCTGTTCG  CCAATGTGCG  CGGCGCACGC  CTGCCGGCCT  GCACGCGGAA  ACCGTGCTCG   60
ATGGCCGTGG  GTTGGGCAAG  GTGCTGAAGC  GCTATCGGAT  TGCGTGAACC  ACTGCAGAGC  120
CGAGCATAGG  CTTATGGGGA  ATCCGCAGCA  ACGGGGTCAG  AGCCCTCTCC  ACAGGAGAGG  180
AATCCGACCC  CAGCGCGATG  AGCCGAGCAT  AGGCTCGTAC  GGGGAATCCG  CAGCAACGGG  240
GTCAGAGCCT  CTCCACAGGA  GAGGAATCCG  ACCCCAGCGC  GANAGGCATA  GGCTCGGCTC  300
TACGGGGAAT  CCGCAGCAAC  GGGGTCAGAG  NNCTCTCCTC  AGGAGAGGCA  TCCGACCCCG  360
GCGCCAGGGC  TTCAGCGCGC                                                  380
```